(12) United States Patent
Tang et al.

(10) Patent No.: US 8,263,018 B2
(45) Date of Patent: Sep. 11, 2012

(54) ENVIRONMENT SENSOR AND CONJUGATED POLYENE FOR MANUFACTURING ENVIRONMENT SENSORS

(75) Inventors: Ben Zhong Tang, Hong Kong (CN); Matthias Haeussler, Hong Kong (CN); Yongqiang Dong, Hong Kong (CN); Hui Tong, Hong Kong (CN)

(73) Assignee: The Hong Kong University of Science and Technology, Kowloon (HK)

(*) Notice: Subject to any disclaimer, the term of this patent is extended or adjusted under 35 U.S.C. 154(b) by 1410 days.

(21) Appl. No.: 11/408,846
(22) Filed: Apr. 21, 2006

(65) Prior Publication Data
US 2006/0240565 A1    Oct. 26, 2006

Related U.S. Application Data

(60) Provisional application No. 60/673,562, filed on Apr. 22, 2005.

(51) Int. Cl.
| | |
|---|---|
| G01N 33/52 | (2006.01) |
| G01N 21/00 | (2006.01) |
| G01N 33/53 | (2006.01) |
| C12Q 1/68 | (2006.01) |
| C08F 220/12 | (2006.01) |

(52) U.S. Cl. ......... 422/401; 422/52; 422/68.1; 422/400; 435/6.1; 435/7.1; 435/7.2; 436/164; 436/172; 526/329.1

(58) Field of Classification Search .................. None
See application file for complete search history.

(56) References Cited

U.S. PATENT DOCUMENTS

| | | | |
|---|---|---|---|
| 4,826,774 A | 5/1989 | Nagel | |
| 5,445,795 A | 8/1995 | Lancaster et al. | |
| 5,519,147 A * | 5/1996 | Swager et al. | 549/59 |
| 5,766,952 A | 6/1998 | Mann et al. | |
| 6,085,576 A * | 7/2000 | Sunshine et al. | 73/29.01 |
| 6,137,118 A | 10/2000 | Kunugi et al. | |
| 6,160,267 A | 12/2000 | Kunugi et al. | |
| 6,338,977 B1 | 1/2002 | Kunugi et al. | |
| 6,417,923 B1 | 7/2002 | Kunugi et al. | |
| 6,578,406 B2 | 6/2003 | Kunugi et al. | |
| 6,822,096 B2 | 11/2004 | Kato | |

OTHER PUBLICATIONS

Song et al., Functional Self-Assembling Bolaamphiphilic Polydiacetylenes as Colorimetric Sensor Scaffolds, Jun. 17, 2004, American Chemical Soceity, vol. 126, pp. 8459-8465.*
Tong, et al., "Protein Detection and Quantitation by Tetraphenylethene-Based Fluorescent Probes with Aggregation-Induced Emission Characteristics", J. Phys. Chem. B, 111, pp. 11817-11823, 2007.
Dong, et al., "Vapochromism and Crystallization-Enhanced Emission of 1,1-Disubstituted 2,3,4,5-Tetraphenylsiloles", J. Inorg. Organomet. Polym., 17, pp. 673-678, 2007.
Dong, et al., "Endowing hexaphenylsilole with chemical sensory and biological probing properties by attaching amino pendants to the silolyl core", Chemical Physics Letters, 446, pp. 124-127, 2007.
Dong, et al., "Aggregation-induced and crystallization-enhanced emissions of 1,2-diphenyl-3,4-bis(diphenylmethylene)-1-cyclobutene", Chem. Commun., pp. 3255-3257, 2007.
Dong, et al., "Aggregation-induced emissions of tetraphenylethene derivatives and their utilities as chemical vapor sensors and in organic light-emitting diodes", Applied Physics Letters, 91, pp. 011111-1-011111-3, 2007.

Tong, et al., "Color-Tunable, Aggregation-Induced Emission of a Butterfly-Shaped Molecule Comprising a Pyran Skeleton and Two Cholesteryl Wings", J. Phys. Chem. B, 111, pp. 2000-2007, 2007.
Tong, et al., "Aggregation-Induced Emission: Effects of Molecular Structure, Solid-State Conformation, and Morphological Packing Arrangement on Light-Emitting Behaviors of Diphenyldibenzofulvene Derivatives", J. Phys. Chem. C, 111, pp., 2287-2294, 2007.
Dong, et al., "Switching the light emission of (4-biphenylyl)phenyldibenzofulvene by morphological modulation: crystallization-induced emission enhancement", Chem. Commun., pp. 40-42, 2007.
Tong, et al., "Molecular packing and aggregation-induced emission of 4-dicyanomethylene-2,6-distyryl-4H-pyran derivatives", Chemical Physics Letters, 428, pp. 326-330, 2006.
Tong, et al., "Fluorescent "light-up" bioprobes based on tetraphenylethylene derivatives with aggregation-induced emission characteristics", Chem. Commun., pp. 3705-3707, 2006.
Hui, et al., "Cyclic Polyenes with Aggregation-Induced Emission Characteristics", Chinese Journal of Luminescence, vol. 27, No. 3, pp. 281-284, Jun., 2006.
Tong, et al., "Tunable aggregation-induced emission of diphenyldibenzofulvenes", Chem. Commun., pp. 1133-1135, 2006.
Chen, et al., "Photoluminescence Spectral Reliance on Aggregation Order of 1,1-Bis(2'-thienyl)-2,3,4,5-tetraphenylsilole", J. Phys. Chem. B, 109, pp. 17086-17093, 2005.
Dong, et al., "Vapochromism of Hexaphenylsilole" Journal of Inorganic and Organometallic Polymers and Materials, vol. 15, No. 2, pp. 287-291, 2005.
Li, et al., "Structural Control of the Photoluminescence of Silole Regioisomers and Their Utility as Sensitive Regiodiscriminating Chemosensors and Efficient Electroluminescent Materials", J. Phys. Chem. B, 109, pp. 10061-10066, 2005.
Chen, et al., "Aggregation-Induced Emission of cis,cis-1,2,3,4-Tetraphenylbutadiene from Restricted Intramolecular Rotation", J. Phys. Chem. A, 108, pp. 7522-7526, 2004. Chen, et al., "Synthesis, Light Emission, Nanoaggregation, and Restricted Intramolecular Rotation of 1,1-Substituted 2,3,4,5-Tetraphenylsiloles", Chem. Mater., 15, pp. 1535-1546, 2003.
Luo, et al., "Aggregation-induced emission of 1-methyl-1,2,3,4,5-pentaphenylsilole", Chem. Commun., pp. 1740-1741, 2001.
Hong, et al., "Aggregation- and Crystallization-Induced Light Emission", Organic Photonic Materials and Devices IX, edited by James G. Grote, et al., Proc. of SPIE vol. 6470, pp. 64700T-1-64700T-12, 12, 2007.
Dong, et al., "Aggregation-induced emission", Organic Light Emitting Materials and Devices X, edited by Zakya H. Kafafi, et al., Proc. of SPIE vol. 6333, pp. 63331D-1-63331D-10, 2006.
Hong, et al., "Synthesis and Aggregation-Induced Emission of Tetraphenylethylene Derivatives and Their Blends With Poly(methyl methacrylate)", Polymer Preprints, 48(2), pp. 367-368, 2007.
Dong, et al., "Aggregation-Induced Emission, Vapochromism and Electroluminescence of Tetraphenylethylene and Its Blends with Poly(methyl methacrylate)", Polymeric Materials: Science & Engineering, 51, pp. 504-505, 2006.
Dong, et al., "Vapochromism of Hexaphenylsilole and Its Blends with Poly(methyl methacrylate)" Polymeric Materials: Science & Engineering, 91, 707-708, 2004.
Dong, et al., "Thermochromism of Hexaphenylsilole and its Blends with Poly(methyl methacrylate)", Polymer Preprints, 45(2), pp. 823-824, 2004.

* cited by examiner

*Primary Examiner* — Neil N Turk

(74) *Attorney, Agent, or Firm* — Nath, Goldberg & Meyer; Jerald L. Meyer

(57) ABSTRACT

The present invention relates to devices for detecting the presence or absence of a target molecule or substance, compounds which may be employed in such devices and methods of using such compounds. In some embodiments, the compounds are conjugated polyenes.

11 Claims, 11 Drawing Sheets

ENVIRONMENT SENSOR AND CONJUGATED POLYENE FOR MANUFACTURING ENVIRONMENT SENSORS

CROSS REFERENCE TO RELATED APPLICATION

Pursuant to 35 U.S.C. §119(e), this application claims priority to U.S. Provisional Application No. 60/673,562, filed Apr. 22, 2005, which is hereby incorporated in its entirety by reference.

FIELD OF THE INVENTION

This invention relates to environmental monitoring technologies. More particularly, it relates to a method of making environmental sensors and to a group of conjugated polyenes with the aggregation-induced emission (AIE) property useful in manufacturing environmental sensors.

BACKGROUND OF THE INVENTION

In our modern society, it has become ever more important for monitoring our environment and providing early sign of environmental changes that may affect health or even life of its inhabitants. With that, there is a growing demand for new technology of making various environmental sensors. Particularly, there is an acute need for sensing environmental hazardous substances such as volatile organic compounds (VOCs). Environmental sensors are also important for quality control in the food, beverage, and fragrance industries, for assessment of odor sources (e.g. wastewater, livestock, and landfill), or for industrial bioprocessings, which often involve organic compound/water mixtures.

Environmental sensors based on detecting fluorescence of an analyte are highly sensitive, thereby lowering detection limits. Different research groups have worked on the development of environmental sensitive sensors for detection of a great variety of organic compounds. For example, James et al. reported the combination of phenyl boronic acids and amine-substituents attached to fluorescent chromophores and utilized this for the detection of different saccharides. Other research groups developed similar sensoric compounds based on this platform (U.S. Pat. Nos. 6,627,177, 6,653,141, 6,673,625, 6,682,938, and 6,916,660). Arimori et al. reported fluorescent sensor molecules based on aliphatic amines with boronic acid and aromatic pendant groups (U.S. Pat. No. 6,740,257). Similarly, Daniloff et al. utilized the interaction of boronic acid and amine substituents of luminescent anthracene and naphthalene compounds for the detection of glucose in the presence of other alpha-hydroxy axids or beta-diketones (U.S. Pat. No. 6,800,451). Covin Jr. et al. utilized some europium-containing indicator monomers in conjunction with a water-soluble polymer (no conjugated polymer was used) for the detection of sugar analytes in environmental samples (U.S. Pat. No. 6,794,195).

Other applications requiring lower detection limits are warfare agents such as organophosphor esters (nerve gas) and nitroaromatics (explosives). Houser et al. utilized dentrimeric siloxane compounds, which are able to recognize the hydrogen-bonding accepting vapors of the warfare agents (U.S. Pat. No. 6,617,040). Similarly, McGill et al. reported linear and branched siloxane polymers, which work in the same way (U.S. Pat. No. 6,630,560).

Yet another field of applications for sensors is the detection of VOCs. The first example of the compounds exhibiting vapochromism were reported in the patent literature by Nagel (U.S. Pat. No. 4,826,774; 1989, Vapochromic double-complex salts). He utilized double complexes salts of platinum and palladium, which upon exposure to organic vapor show a color as well as a fluorescence change.

Lancaster et al. (U.S. Pat. No. 5,445,785; Volatile organic compound sensing devices) fabricated various apparatus using vapochromic substances having a composition of an inorganic double-complex salt. He apparently have not specified or included any structures or chemical composition into his patent.

Later, Mann et al. (U.S. Pat. No. 5,766,952; 1998, Vapochromic platinum-complexes and salts) invented platinum-platinum double complex salts and neutral platinum complexes, which exhibit again a change in color and luminescence.

More recently, Kato (U.S. Pat. No. 6,822,096; 2004, Environmental-sensitiv luminescent dimine-platinum binuclear complexes), utilized binuclear platinum (II) complexes, which did not only show a dark-red/light-red change of color but also a near-infrared/red change of luminescence via reversible adsorption of vapor of acetonitrile or ethanol, and therefore permitted the observation of on-off change of visually effective luminescence.

Other patents known to the applicants (U.S. Pat. Nos. 6,578,406; 6,338,977; 6,160,267 Vapochromic LED; U.S. Pat. Nos. 6,417,923; and 6,137,118 Vapochromic Photodiode) were all based on the platinum compounds described in U.S. Pat. No. 5,766,952 and described the fabrication of different devices utilizing the vapochromic behavior.

Many of the previously reported fluorescent materials focused on the detection of saccharides by the competing intramolecular interaction of an amine functionality with the boronic acid pendant. Less effort was spend on other biological compounds. Furthermore, the vapor-sensing compounds and devices are often manufactured from the expensive platinum salts and complexes and/or in combination with palladium. They based mainly on a color shift from dark-red to light-red, making it difficult to sense only by the eye. Sensors exhibiting an on-off change in their luminescent color rather then a color shift will be thus not only advantageous but also more sensitive. To applicants' knowledge the only known "on-off" example was shown by Kato (U.S. Pat. No. 6,822, 096), who utilized the luminescence change from the invisible near-infrared to the visible red of binuclear platinum (II) complexes. Although these complexes seem to be an "on-off" sensor for the human eye, it only shifts the emitted wavelength out of the visible spectrum.

SUMMARY OF THE INVENTION

As an object of the present invention, there is provided a group of novel conjugated luminescent polyenes which are useful in fabricating various environmental sensors. The emission color of these new polyenes ranges from blue to red arising from the different chromophoric structures. They show an aggregation-induced emission (AIE) phenomenon that is increased fluorescence upon addition of miscible non-solvent such as water to acetone or ethanol solutions of the polyenes or simply enhanced emission of the solid state compared with their dilute organic solutions. The AIE effect might be caused by enhanced intermolecular interaction and/or restricted rotation of attached aromatic moieties.

This AIE effect also works in the presence of volatile organic compounds (VOCs). The emission of the polyene nanocrystals and thin films coated on TLC plates are quenched upon exposure to VOCs and become visibly emissive again when the VOCs are removed. Depending on the chromophoric structure incorporated, this process is fully reversible with a plurality of repeating cycles. The luminescence quenching in the presence of volatile organic vapor provides a real reversible "on-off" switch, making it highly sensitive for the use in detection devices.

Furthermore, they are organic compounds, which make them easily accessible and much more ecumenical compared to their platinum or transition metal-containing counterparts.

In contrast to the conventional AIE behavior, sterically hindered siloles exhibit intense fluorescence in dilute organic solution, which in the presence of explosives such as nitroanilines, rapidly fades away. This emission-quenching can not only be highly efficient but can even distinguish between the different isomers, making them promising candidates for warfare detection systems. Mixing water-soluble polyenes with natural occurring compounds such as proteins (e.g. BSA) leads to an agglomeration of the amphiphilic dyes in the hydrophobic pockets and thus to an enhanced emission.

The AIE feature makes thus the new polyenes excellent candidates for the usage of various sensor and detection devices.

The novel polyene of the present invention comprising a backbone formula selected from the group consisting of:

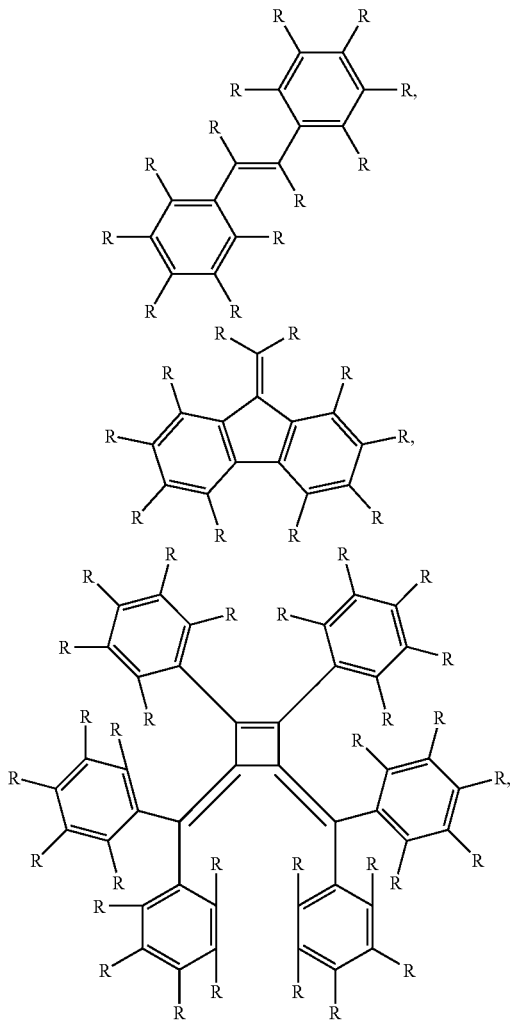

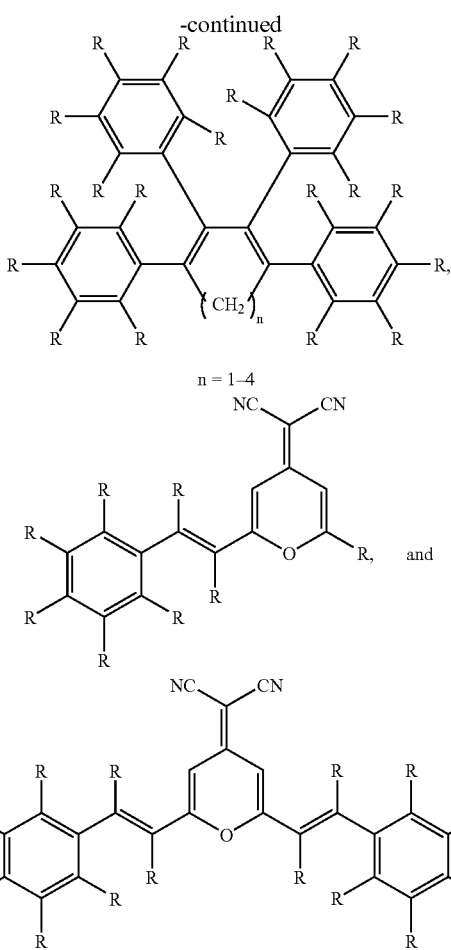

wherein R is a substituent independently selected from the group consisting of H, C(O)R, COOR, $BR_2$, $SiR_3$, $GeR_3$, $NR_2$, $PR_2$, $P(O)R_2$, OR, SR, SeR, alkyl, unsaturated alkyl, heteroalkyl, cycloalkyl, heterocycloalkyl, aryl, and heteroaryl wherein said alkyl, unsaturated alkyl, heteroalkyl, cycloalkyl, heterocycloalkyl, aryl, and heteroaryl are independently either substituted or unsubstituted.

As another object of the present invention, there is provided a method for detecting environmental changes, comprising a step of using linear, cyclic, or combination of both linear and cyclic π-conjugated organic compounds, which include, but are not limited to, the above specified compounds. These π-conjugated organic compounds (polyenes) contain one or more chromophores such as, for example, siloles, butadienes, cyclobutadienes, cyclcobutenes, fulvenes, and 4H-pyrans. These compounds are highly luminescent with their emitted light ranging from blue to red, depending on their structure. Their luminescent behavior features the aggregation-induced emission (AIE) phenomenon, which turns the dyes from faint-emitters when molecularly dissolved into strong luminophors when aggregated or in solid state.

The various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated and described preferred embodiments of the invention.

DETAILED DESCRIPTION OF PARTICULAR EMBODIMENTS

Figure 1:
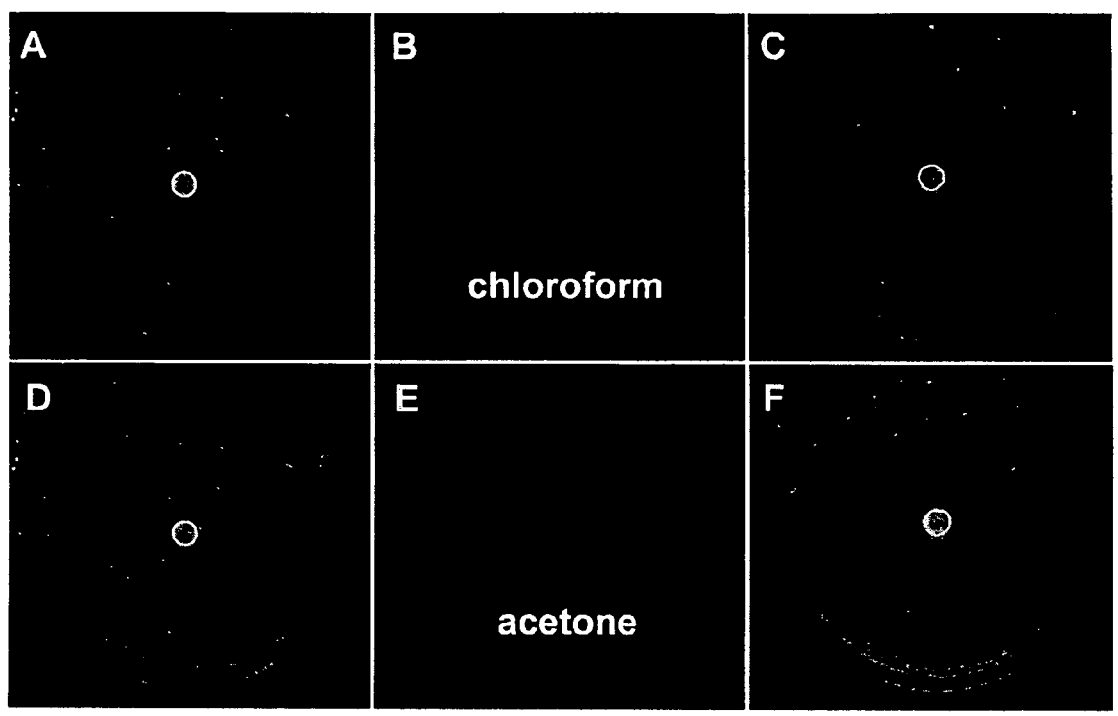
FIG. 1 shows photos of the T2TPS spots on the TLC plates in the Petri dish sets in the absence (A and D) and presence (B and E) of vapors of organic solvents and their recovery after removing the solvents (C and F).

The following definitions are provided for the purpose of understanding the present invention and for constructing the appended patent claims.

"Conjugated double bonds" mean one or more covalent double bonds in a molecule where the single and double bonds alternate.

"A chemically conjugated system" means a system of atoms covalently bonded with alternating single and double bonds in a molecule of an organic compound.

"A polyene" means a molecule of an organic compound containing more than one alkene. For example, a diene has two C=C; a triene has 3 C=C; etc.

"Target molecule" means the molecule whose changes in concentration in an environment are intended to be detected by a sensor. "Detecting molecule" means a molecule which, upon contacting with a target molecule in the environment, can provide a signal perceivable to human.

"Alkyl" means, unless otherwise specified, an aliphatic hydrocarbon group which may be straight or branched chain having about 1 to about 15 carbon atoms in the chain, optionally substituted by one or more halogen atoms. A particularly suitable alkyl group has from 1 to about 6 carbon atoms. The term "unsaturated" refers to the presence of one or more double and triple bonds between atoms of a radical group, for example.

"Heteroatom" means an atom selected from the group consisting nitrogen, oxygen, sulphur, phosphorus, boron and silicon.

"Heteroaryl" as a group or part of a group denotes an optionally substituted aromatic monocyclic or multicyclic organic moiety of about 5 to about 10 ring members in which at least one ring member is a heteroatom.

"Cycloalkyl" means an optionally substituted non-aromatic monocyclic or multicyclic ring system of about 3 to about 10 carbon atoms.

"Heterocycloalkyl" means a cycloalkyl group of about 3 to 7 ring members in which at least one ring member is a heteroatom.

"Aryl" as a group or part of a group denotes an optionally substituted monocyclic or multicyclic aromatic carbocyclic moiety of about 6 to about 14 carbon atoms, such as phenyl or naphthyl.

"Heteroalkyl" refer to alkyl in which at least one carbon atom is replaced by a heteroatom.

I. Synthesis of Conjugated Polyene

Scheme of Synthesis of Silole Derivatives

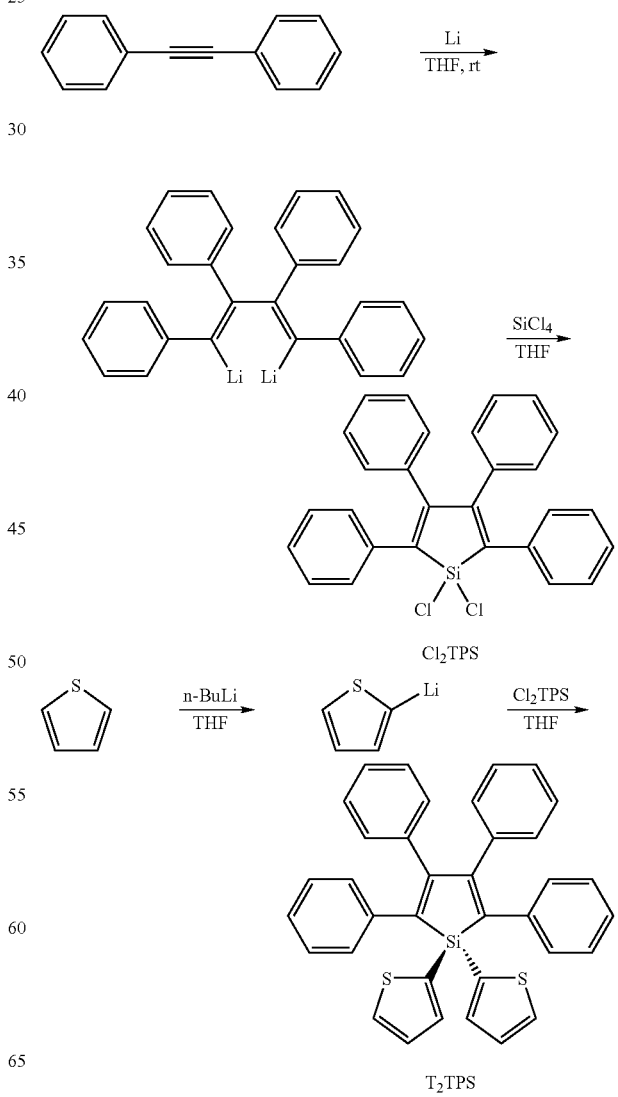

7
-continued
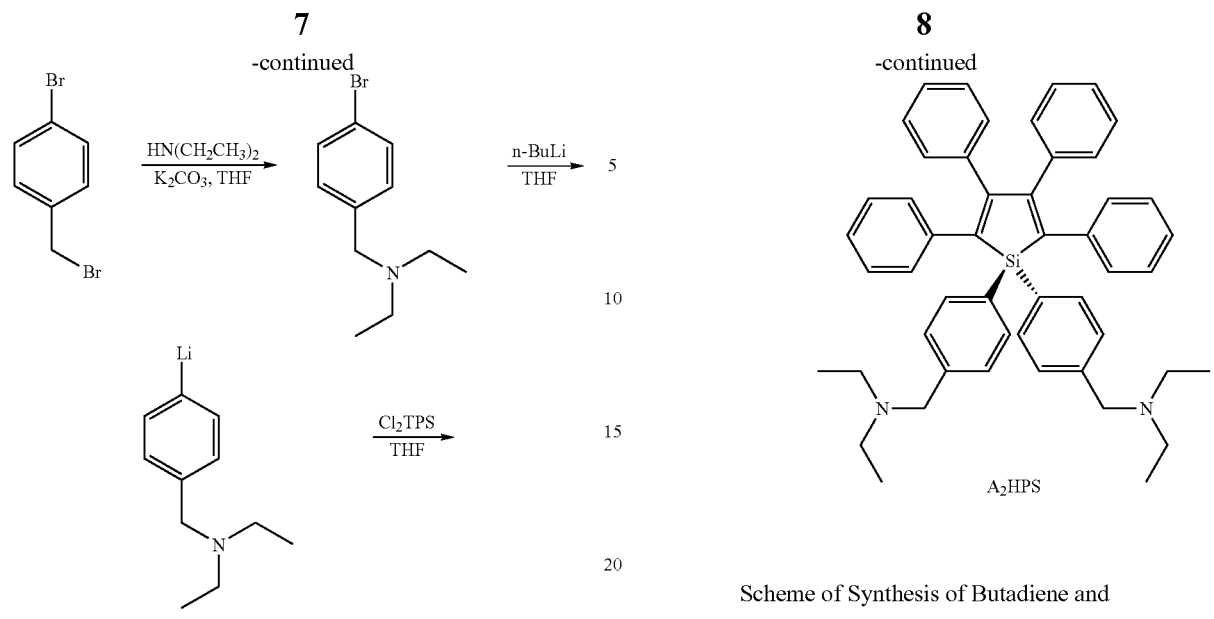
8
-continued
Scheme of Synthesis of Butadiene and Cyclobutadiene Derivatives
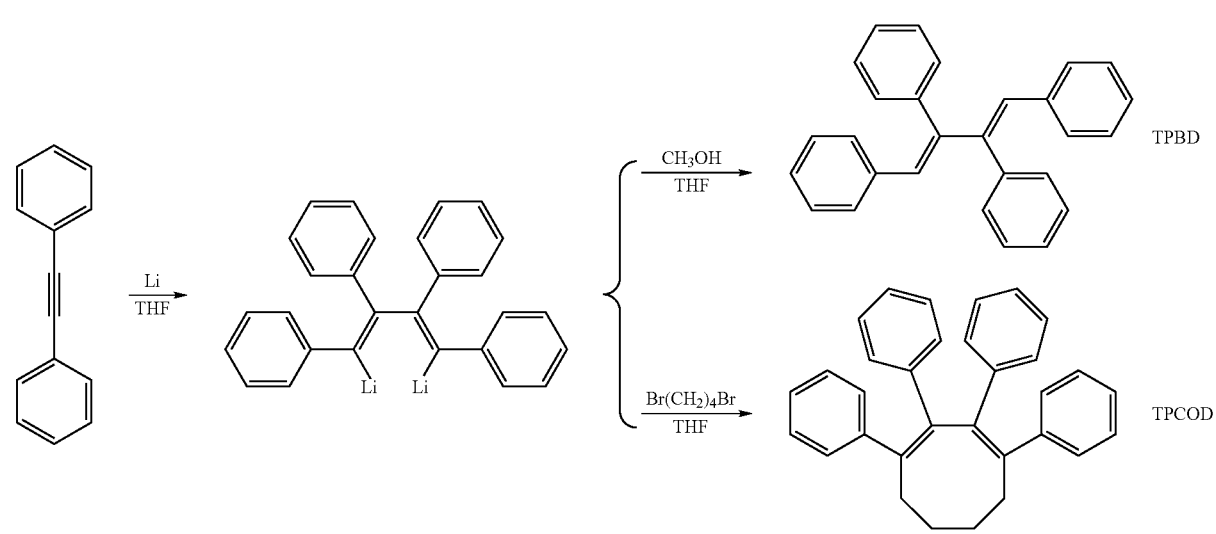
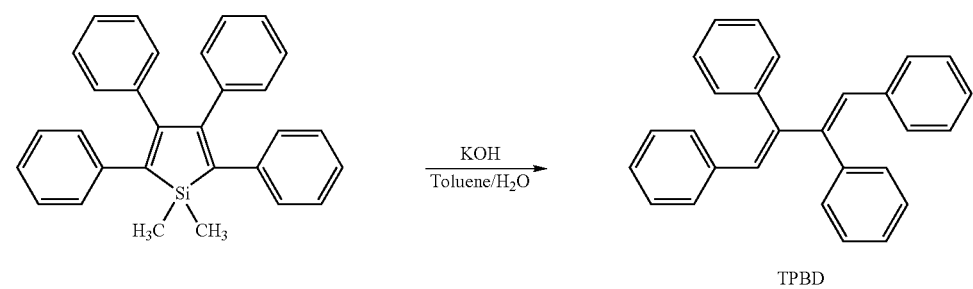

Scheme of Synthesis of Fulvene Derivatives

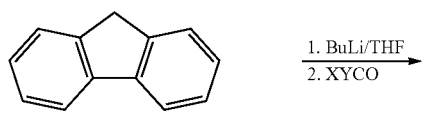

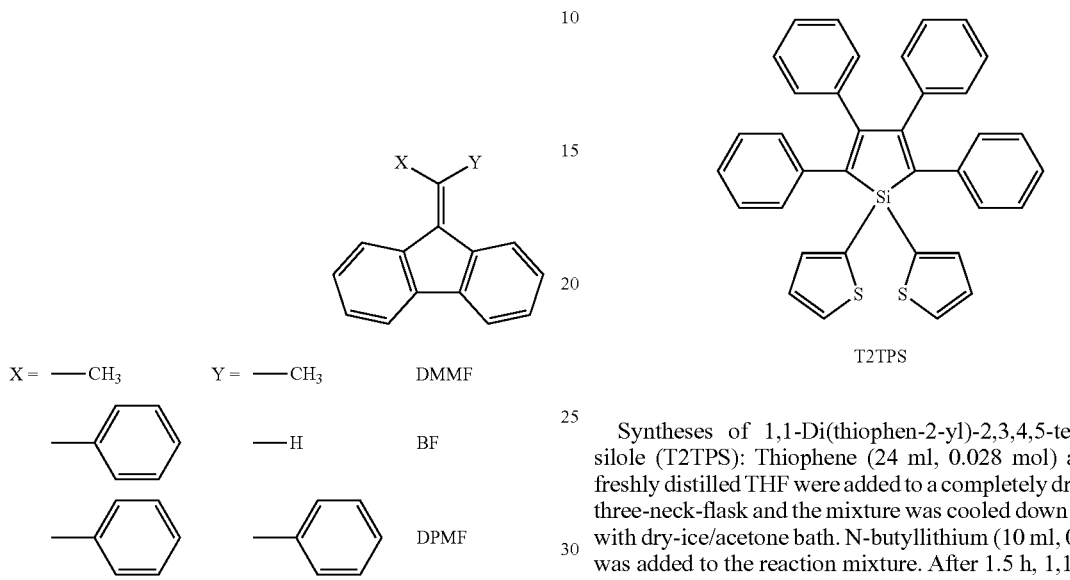

Scheme of Synthesis of Diphenylethylene Derivatives

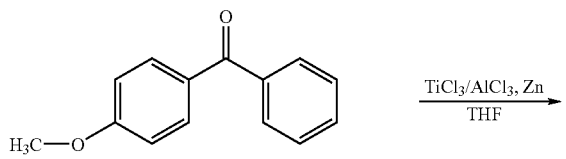

Obviously, by using properly substituted versions of the precursors in the above schemes, people of ordinary skill in the art are able to synthesize corresponding substituted products.

EXAMPLE 1

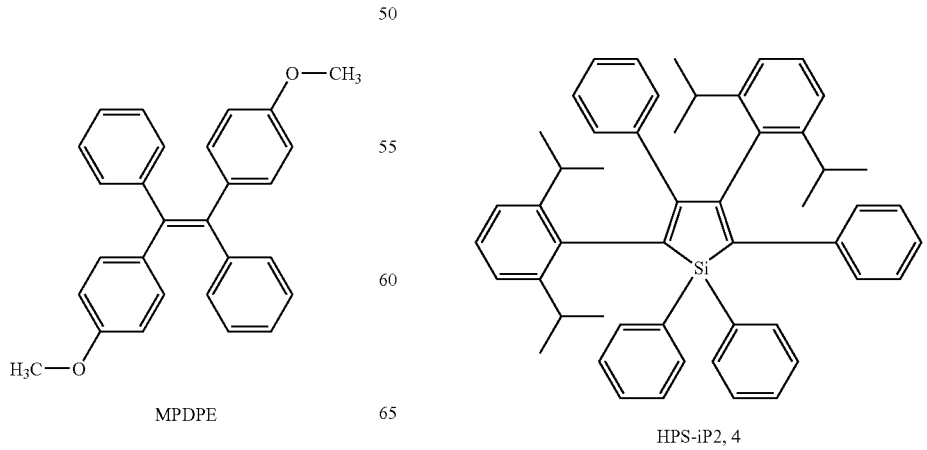

Syntheses of 1,1-Di(thiophen-2-yl)-2,3,4,5-tetraphenyl-silole (T2TPS): Thiophene (24 ml, 0.028 mol) and 80 ml freshly distilled THF were added to a completely dried 250 ml three-neck-flask and the mixture was cooled down to −78° C. with dry-ice/acetone bath. N-butyllithium (10 ml, 0.025 mol) was added to the reaction mixture. After 1.5 h, 1,1-dichloro-2,3,4,5-tetraphenylsilole (4.54 g, 0.01 mol), dissolved in 50 ml THF, was dropwise added. The temperature was kept at −78° C. for another 1 h before it was allowed to warm to room temperature. The reaction mixture was refluxed for 12 h and afterwards quenched by the addition of water. THF was removed under reduced pressure and diethyl ether was used to extract the water phase three times. The combined organic phases were dried over $MgSO_4$ and purified by column chromatography (hexane/$CHCl_3$ 3:1). mp 212-213° C. $^1$H NMR (300 MHz, $CDCl_3$): 7.68 (d, 2H), 7.47 (d, 2H), 7.20 (m, 2H), 7.06-6.80 (m, br, 20H). $^{13}$C NMR (75 MHz, $CDCl_3$), δ (TMS, ppm): 156.9, 139.3, 139.0, 133.7, 130.5, 130.2, 130.0, 129.1, 128.4, 128.1, 127.1, 126.5. UV (THF, $4.0 \times 10^{-5}$ mol/L), $\lambda_{max}$ (nm): 370. MS (CI): m/e calcd for $C_{36}H_{26}S_2Si$ 550.1, found 550.0 ($M^+$)

EXAMPLE 2

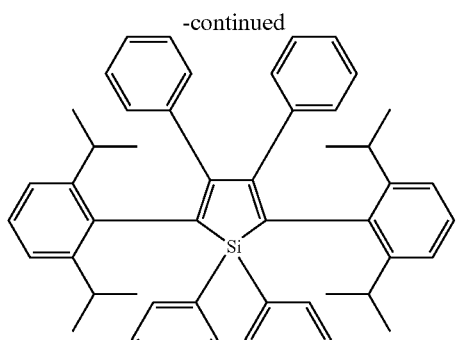

HPS-iP2, 5

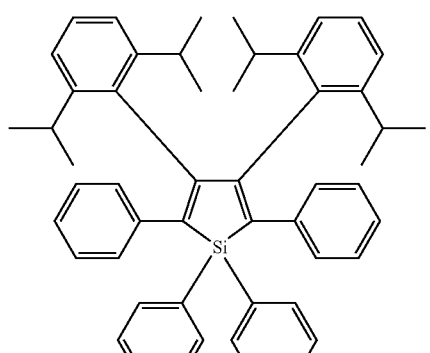

HPS-iP3, 4

Syntheses of Regioisomers of HPS-iPx,y: 2,4-Bis(2,6-diisopropyl)phenyl-1,1,3,5-tetraphenylsilole (HPS-iP2,4), 2,5-Bis(2,6-diisopropyl)-phenyl-1,1,3,4-tetraphenylsilole (HPS-iP2,5) and 3,4-Bis(2,6-diisopropyl)phenyl-1,1,2,5-tetraphenylsilole (HPS-iP3,4). Under dry nitrogen, 141.7 mg of freshly cut lithium shavings (20.42 mmol) was added to a solution of 1-(2-(2,6-diisopropylphenyl)ethynyl)benzene (5.35 g, 20.42 mmol) in 18 mL of THF at room temperature. The mixture was cooled to, and stirred at, 0° C. for 5 h and was then warmed to, and stirred at, room temperature for 16 h. The lithiation mixture was added dropwise to a solution of dichlorodiphenylsilane (1.5 mL, 7.08 mmol) in 120 mL of THF over 2 h. The resultant mixture was stirred at room temperature for 5 h and then refluxed for 18 h. The solvent was evaporated and the crude product was purified on an alumina column using hexane as the eluent. The silole regioisomers were isolated and purified by repeated chromatographic separations on alumina columns using hexane as the eluent. After ~20-times column purifications, 400 mg of HPS-iP2,4, 23 mg of HPS-iP2,5 and 10 mg of HPS-iP3,4 were finally obtained as yellow-green solids.

Characterization data of HPS-iP2,4: $^1$H NMR (300 MHz, CDCl$_3$), δ (TMS, ppm): 7.69 (d, 4H, Ar—H), 7.29 (m, 6H, Ar—H), 7.10 (d, 2H, Ar—H), 6.86 (m, br, 14H, Ar—H), 3.34 (m, 2H, CH of iPr at Ar-4), 2.89 (m, 2H, CH of iPr at Ar-2), 0.98 (m, 12H, CH$_3$ of iPr at Ar-4), 0.69 (d, 6H, CH$_3$ of iPr at Ar-2 towards Ar-3 side), 0.18 (d, 6H, CH$_3$ of iPr at Ar-2 towards Ar-1 side). $^{13}$C NMR (75 MHz, CDCl$_3$), δ (TMS, ppm): 147.1, 146.2, 136.7, 132.6, 130.9, 130.7, 130.5, 128.9, 128.4, 127.2, 126.9, 124.2, 123.5, 32.1, 31.7, 25.3, 24.9, 24.6, 24.2. MS (CI): m/e calcd for C$_{52}$H$_{54}$Si 706.4, found 706.3 (M$^+$). UV (acetone, 1×10$^{-5}$M), λ$_{max}$: 367 nm.

HPS-iP2,5: $^1$H NMR (300 MHz, CDCl$_3$), δ (TMS, ppm): 7.57 (d, 4H, Ar—H), 7.35 (m, 4H, Ar—H), 7.29 (d, 4H, Ar—H), 7.06 (m, 4H, Ar—H), 6.84 (m, br, 10H, Ar—H), 3.26 (m, 2H, CH of iPr at Ar-2 and -5 on Ar-3 and -4 sides), 2.89 (m, 2H, CH of iPr at Ar-2 and -5 on Ar-1 side), 0.98 (m, 12H, CH$_3$ of iPr at Ar-2 and -5 on Ar-3 and -4 sides), 0.73 (m, 12H, CH$_3$ of iPr at Ar-2 and -5 on Ar-1 side). $^{13}$C NMR (75 MHz, CDCl$_3$), δ (TMS, ppm): 147.1, 146.7, 146.0, 136.6, 132.7, 131.0, 130.4, 130.2, 129.1, 128.9, 127.2, 126.9, 124.1, 123.4, 123.0, 32.1, 31.7, 30.7, 25.4, 25.0, 24.6, 24.2, 23.0. MS (CI): m/e calcd for C$_{52}$H$_{54}$Si 706.4, found 706.5 (M$^+$). UV (acetone, 1×10$^{-5}$ M), λ$_{max}$: 378 nm.

HPS-iP3,4: $^1$H NMR (300 MHz, CDCl$_3$), δ (TMS, ppm): 7.90 (d, 4H, Ar—H), 7.43 (m, 6H, Ar—H), 7.10 (d, 2H, Ar—H), 7.02 (d, 2H, Ar—H), 6.89 (m, br, 12H, Ar—H), 3.00 (m, 4H, CH of iPr), 0.75 (d, 12H, CH$_3$ of iPr at Ar-3 and -4 positioned outwards), 0.46 (d, 12H, CH$_3$ of iPr at Ar-3 and -4 positioned inwards). $^{13}$C NMR (75 MHz, CDCl$_3$), δ (TMS, ppm): 147.2, 137.2, 136.6, 130.7, 130.5, 128.9, 128.8, 128.3, 126.9, 124.2, 123.5, 32.1, 31.6, 25.8, 24.9, 24.6, 24.3. MS (CI): m/e calcd for C$_{52}$H$_{54}$Si 706.4, found 706.4 (M$^+$). UV (acetone, 1×10$^{-5}$ M), λ$_{max}$ 388 nm.

EXAMPLE 3

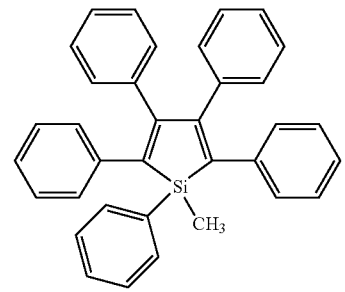

PMS

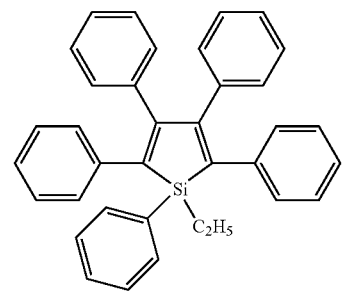

PES

The synthesis of 1-Phenyl-1-methyl-2,3,4,5-tetraphenylsilole (PMS) and 1-phenyl-1-ethyl-2,3,4,5-tetraphenylsilole (PES) were carried out according to Example 2 by using the corresponding methyl and ethyl substituted phenylsilyldichlorides.

Characterization Data:

PMS: $^1$H NMR (300 MHz, CDCl$_3$): δ(TMS, ppm): 7.68 (m, 2H), 7.39 (m, 3H), 7.04 (m, 12H), 6.88 (m, 8H), 0.81 (s, 3H).

PES: mp 175-177° C. $^1$H NMR (300 MHz, CDCl$_3$): 7.78 (d, 2H), 7.37 (m, 3H), 7.03-6.85 (m, br, 20H), 2.70 (s, 1H). $^{13}$C NMR (75 MHz, CDCl$_3$), δ (TMS, ppm): 157.1, 138.5, 138.0, 136.5, 135.0, 130.5, 130.0, 129.7, 129.2, 128.4, 127.8, 127.6, 126.7, 126.0, 98.6, 82.5. UV (THF, 4.0×10$^{-5}$ mol/L), λ$_{max}$ (nm): 372.

EXAMPLE 4

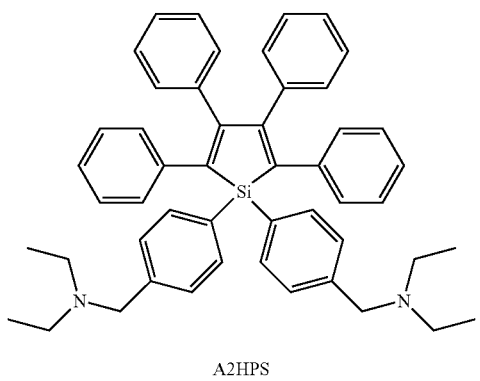

A2HPS

The synthesis of the diamine substituted silole was carried out similarly to Example 1.

Characterization Data:

A$_2$HPS: mp 119-120° C. $^1$H NMR (300 MHz, CDCl$_3$): 7.56 (d, 2H), 7.32 (d, 2H), 7.05-6.75 (m, br, 20H), 3.55 (s, 4H), 2.54 (m, 8H), 1.04 (m, 12H). $^{13}$C NMR (75 MHz, CDCl$_3$), δ (TMS, ppm): 156.6, 142.3, 140.0, 139.9, 139.0, 136.2, 130.2, 129.8, 129.0, 127.9, 127.6, 126.5, 125.7, 57.8, 47.2, 12.1. MS (CI): m/e calcd for C$_{50}$H$_{52}$N$_2$Si, 708.4, found 709.4 (M$^+$). UV (THF, 4.0×10$^{-5}$ mol/L), λ$_{max}$(nm): 364.

EXAMPLE 5

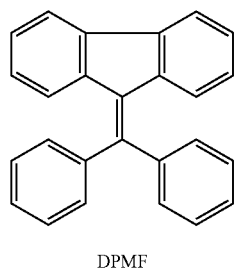

DPMF

Syntheses of 9-(Diphenylmethylene)fluorene (DPMF): Fluorene (3.33 g, 0.02 mol) and 100 ml freshly distilled THF were added to a completely dried 250 ml two-neck-flask and the mixture was cooled down to −78° C. with dry-ice/acetone bath. N-butyllithium (16 ml, 0.04 mol) was added to the reaction mixture. After 1.5 h, benzophenone (3.64 g, 0.02 mol), dissolved in 30 ml THF, was dropwise added. The temperature was kept at −78° C. for another 1 h before it was allowed to slowly warm to room temperature. After 12 h, the reaction was quenched by the addition of water. THF was removed by reduced pressure and diethyl ether was used to extract the water phase three times. The combined organic phases were dried over MgSO$_4$ and purification by column chromatography (hexane/CHCl$_3$ 3:1) yielded light-yellow transparent crystals (2.9 g, 43%). mp 228-229° C. $^1$H NMR (300 MHz, CDCl$_3$): δ (TMS, ppm): 7.68 (d, 2H), 7.37 (s, 10H), 7.21 (m, 2H), 6.90 (m, 2H), 6.21 (d, 2H). $^{13}$C NMR (75 MHz, CDCl$_3$): δ (TMS, ppm): 145.6, 143.1, 140.7, 138.9, 134.4, 129.9, 129.0, 128.4, 127.8, 126.6, 125.1, 119.5.

EXAMPLE 6

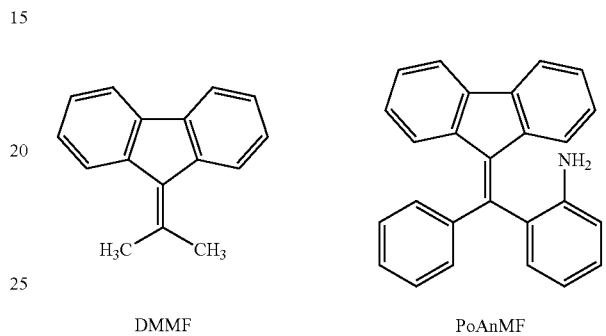

DMMF                    PoAnMF

The synthesis of 9-(dimethylmethylene)fluorene (DMMF) and {9-phenyl-9-(2-aminophenyl)methylene]fluorene (PoAnMF) was carried out similarly to Example 5.

Characterization Data:

DMMF: mp 111-112° C. $^1$H NMR (300 MHz, CDCl$_3$): δ (TMS, ppm): 7.81 (m, 2H), 7.75 (m, 2H), 7.28 (m, 4H), 2.53 (s, 6H). $^{13}$C NMR (75 MHz, CDCl$_3$), δ (TMS, ppm): 141.6, 140.2, 139.7, 132.9, 127.3, 126.9, 125.6, 120.0, 27.1. MS (CI): m/e calcd for C$_{16}$H$_{14}$ 206.1, found 206.1 (M$^+$)

PoAnMF: M.p.: 188-190° C. $^1$H NMR (300 MHz, CDCl$_3$), δ (ppm): 7.70 (d, 2H), 7.49-7.41 (m, 5H), 7.31-7.19 (m, 3H), 7.10 (d, 1H), 7.01 (t, 1H), 6.94 (t, 1H), 6.85-6.73 (m, 4H), 3.82 (s, 2H). $^{13}$C NMR (75 MHz, CDCl$_3$), δ (ppm): 143.7, 142.2, 141.9, 140.8, 140.4, 138.5, 138.1, 135.2, 130.4, 129.5, 129.0, 128.5, 128.2, 128.0, 127.3, 126.6, 125.2, 124.4, 119.4, 119.3, 116.2. FAB mass spectrum m/e: 345.1 ([M]$^+$ calcd. 345.2).

EXAMPLE 7

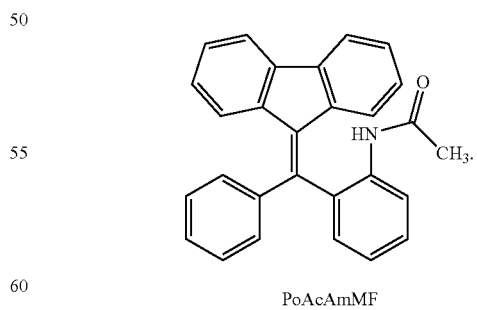

PoAcAmMF

Synthesis of PoAcAmMF: PoAnMF (0.5 g), acetic acid (0.1 g), and 4-(dimethylamino)pyridine (0.1 g) were dissolved in 100 mL of dry dichloromethane in a 250 mL two-necked flask under nitrogen. The solution was cooled to 0-5° C. with an ice-bath, to which 0.48 g dicyclohexylcarbodiimide in 50 mL of dichloromethane was added under stirring via a dropping funnel with a pressure equalization arm. The mixture was stirred at room temperature overnight. The solution was concentrated by a rotary evaporator. The crude product was purified by a silica gel column using hexane and chloroform (3:1) as the eluent. The product was obtained as white needle crystal. The yield was 57%. M.p. 248-250° C. (decomp.) $^1$H NMR (300 MHz, CDCl$_3$), δ (ppm): 8.25 (d, 1H), 7.68 (d, 2H), 7.45-7.41 (m, 6H), 7.28-7.15 (m, 5H), 6.94 (t, 2H), 6.80 (d, 1H), 6.51 (d, 1H), 3.73 (s, 1H), 1.80 (s, 3H). $^{13}$C NMR (75 MHz, CDCl$_3$), δ (ppm): 168.6, 141.6, 141.3, 141.0, 140.3, 138.3, 138.1, 137.0, 135.5, 130.8, 130.0, 129.3, 129.0, 128.9, 127.8, 127.2, 125.6, 125.5, 125.0, 122.7, 120.0, 119.9, 31.0. FAB mass spectrum m/e: 388.2 ([M+H]$^+$ calcd. 388.2).

EXAMPLE 8

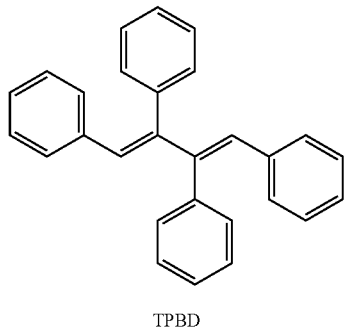

TPBD

Syntheses of (1E,3E)-1,2,3,4-Tetraphenylbuta-1,3-diene (TPBD): A mixture of 1,1-dimethyl-2,3,4,5-tetraphenylsilole (1.24 g, 3 mmol) and potassium hydroxide (1.68 g, 30 mmol) in toluene/water 2:1 mixed solvent (15 mL) was heated to reflux for 20 h. After dilution with an aqueous solution of HCl (0.1 N), the mixture was extracted with ether several times. The combined extract was washed with brine, dried over anhydrous MgSO$_4$, and concentrated. Recrystallization from a toluene/heptane mixture afforded TPBD in 63% yield. White solids; mp=183-184° C. $^1$H NMR (300 MHz, CDCl$_3$) δ (TMS, ppm): 7.44-7.23 (m, 10H), 6.99 (m, 6H), 6.72 (m, 4H), 6.28 (s, 2H); $^{13}$C NMR (75 MHz, CDCl$_3$) δ (TMS, ppm): 145.3, 139.6, 137.1, 131.5, 130.2, 129.4, 128.7, 127.7, 127.2, 126.5.

EXAMPLE 9

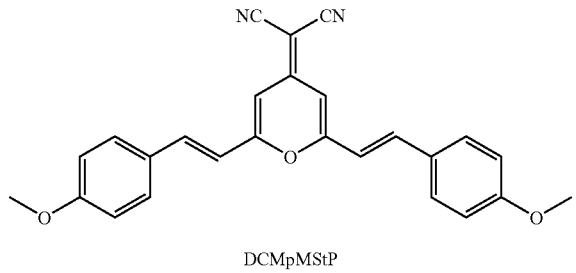

DCMpMStP

Synthesis of DCMpMStP: A mixture of 4-methoxyl-benzaldehyde (0.38 g), 4-dicyanomethylene-2,6-dimethyl-4H-pyran (0.06 g), piperidine (10 drops), and freshly distilled acetonitrile (60 mL) were refluxed under argon for 24 h. The reaction mixture was cooled to room temperature. The yellow precipitate was filtered and washed with 50 mL of acetonitrile. The crude product was purified by recrystallization from acetone/methanol to afford a yellow solid with a yield of 52%. M.p. 240.2-242.6° C. $^1$H NMR (CDCl$_3$, 300 MHz) δ (TMS, ppm): 7.55-7.51 (d, 5H), 7.46 (s, 1H), 6.97 (d, 4H), 6.79 (s, 1H), 6.66 (s, 3H), 6.60 (s, 1H), 3.88 (s, 6H). $^{13}$C NMR (CDCl$_3$, 75 MHz) δ (TMS, ppm): 159.1, 155.7, 137.7, 130.3, 129.6, 128.2, 116.3, 114.8, 106.6, 93.6, 55.6. MS (FAB): m/e 408.7 ([M+H]$^+$).

EXAMPLE 10

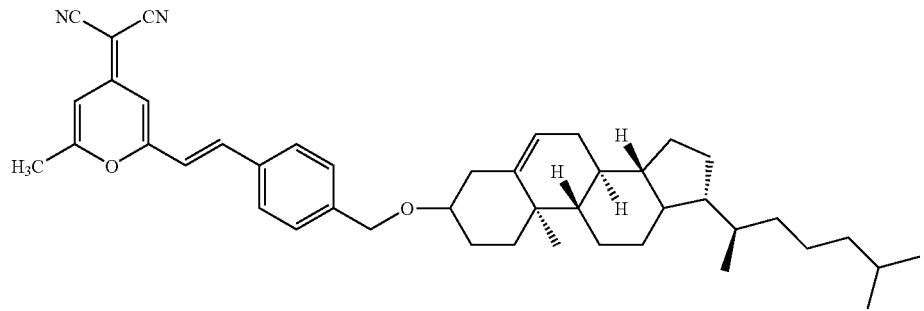

SCholP

Syntheses of 2-(2-(4-(((8R,9R, 10S,13S,14R,17S)-2,3,4,7,8,9,10,11,12,13,14,15,16,17-Tetradecahydro-10,13-dimethyl-17-((S)-6-methylheptan-2-yl)-1H-cyclopenta[a]phenanthren-3-yloxy)methyl)styryl)-6-methyl-4H-pyran-4-ylidene)malononitrile (SCholP): A mixture of 4-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxymethyl]-benzaldehyde (3.05 g, 5.8 mmol), 2-(2,6-dimethylpyran-4-ylidene)-malononitrile (1.0 g, 5.8 mmol), piperidine (10 drops), and freshly distilled acetonitrile (20 mL) were refluxed under nitrogen for 24 h. The reaction mixture was cooled to room temperature. The yellow precipitate was filtered and washed with 50 mL of acetonitrile. The crude product was purified by recrystallization from THF/methanol to afford a yellow solid with a yield of 51%; mp=231-232° C. $^1$H NMR (300 MHz, CDCl$_3$) δ (TMS, ppm): 7.59 (d, 2H), 7.47 (d, 2H), 6.78 (s, 1H), 6.74 (s, 1H); 6.70 (s, 2H); 5.37 (d, 1H), 4.61 (s, 2H), 3.30 (m, 1H), 2.41 (m, 2H), 1.96 (m, 6H), 1.55-0.85 (m, 35H), 0.68(s, 3H), $^{13}$C NMR (75 MHz, CDCl$_3$) δ (TMS, ppm): 158.3, 142.1, 140.9, 137.9, 133.7, 128.2, 128.0, 121.9, 118.4, 115.2, 107.3, 79.1, 69.5, 56.9, 56.3, 50.3, 42.4, 39.9, 39.6, 39.3, 37.3, 36.3, 35.9, 32.1, 32.0, 28.6, 28.3, 28.1, 24.4, 23.9, 22.9, 22.7, 21.2, 19.5, 18.8, 12.0. mass spectrum m/e: 659.4 ([M+H]$^+$ calcd. 659.5).

EXAMPLE 11

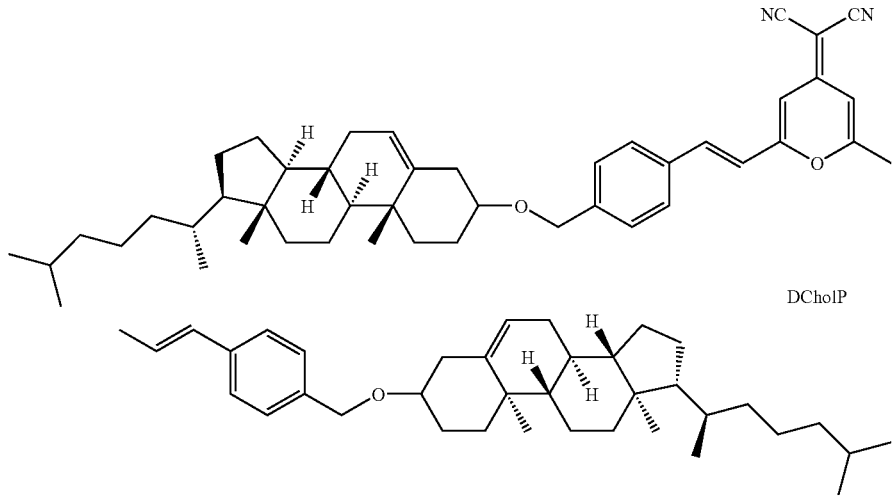

DCholP

Synthesis of DcholP: A mixture of 4-((cholesteryloxy)methyl)benzaldehyde (0.38 g), 4-dicyanomethylene-2,6-dimethyl-4H-pyran (0.06 g), piperidine (10 drops), and freshly distilled acetonitrile (60 mL) were refluxed under argon for 24 h. The reaction mixture was cooled to room temperature. The yellow precipitate was filtered and washed with 50 mL of acetonitrile. The crude product was purified by recrystallization from dichloromethane/methanol to afford a yellow solid with a yield of 52%. M.p. 239-240° C. $^1$H NMR (CDCl$_3$, 300 MHz, ppm): δ 7.58-7.55 (d, 5H), 7.50 (s, 1H), 7.45-7.42 (d, 4H), 6.79 (s, 1H), 6.74(s, 1H), 6.70 (s, 2H), 5.36 (d, 2H), 4.61 (s, 4H), 3.30 (m, 2H), 2.46-1.87 (m, 16H), 1.55-0.68 (m, 70H). MS: $^{13}$C NMR (CDCl$_3$, 75 MHz, ppm): δ 158.3, 142.1, 140.9, 137.9, 133.7, 128.2, 128.0, 121.9, 118.4, 115.2, 107.3, 79.1, 69.5, 56.9, 50.3, 42.4, 39.9, 39.6, 39.3, 37.3, 36.3, 35.9, 32.1, 32.0, 28.6, 28.3, 28.1, 24.4, 23.9, 22.9, 22.7, 21.2, 19.5, 18.8, 12.0. FAB mass spectrum m/e: 1146.3 ([M+H]$^+$ calcd. 1146.7).

EXAMPLE 12

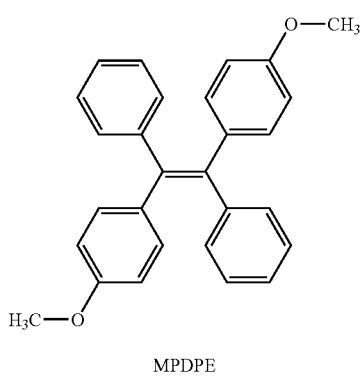

MPDPE 1,2-bis(4-methoxylphenyl)-1,2-diphenylethene (MPDPE) A suspension of 1.06 g (5.0 mmol) p-methoxylbenzophenone, 5.81 g (6.7 mmol, 1.34 equiv.) TiCl$_3$/AlCl$_3$, 8.01 g (122.0 mmol, 25 eq) Zn dust in 100 ml dry THF was refluxed for 20 h. The reaction mixture was cooled to room temperature and filtered. The filtrates were evaporated. The crude product was purified by a silica-gel column using hexane as eluent. Yield 91%. $^1$H NMR (CDCl$_3$, 300 MHz) δ (ppm): 7.10-7.06 (m, 10H), 6.93 (t, 4H), 6.64 (t, 4H), 3.74 (s, 6H). $^{13}$C NMR (CDCl$_3$, 75 MHz) δ (ppm): 158.0, 144.4, 139.7, 136.5, 132.6, 131.5, 127.8, 126.3, 113.2, 55.2. MS (TOF) m/e: 392.1 (M$^+$, calcd. 392.2).

EXAMPLE 13

Measurment of luminescence of polyene films on TLC plates: TLC aluminium plates (MERCK, Silica 60 F$_{254}$) with a size of 15 mm×45 mm were used. After diminishing free particles on the TLC plates by compressed air, the plates were put into a bottle for developing. Chloroform solutions of siloles with a concentration of 2 mg/mL were used as developing liquids. Silole films of about 15 mm×44 mm were prepared. In the specimen chamber of a SLM 8000C spectrofluorometer, the TLC films were excited at an angle of 45°, and the emission light was detected at 135°, so the emission light perpendicular to emission lights were recorded on the spectrofluorometer.

II. Utilities of Conjugated Polyene as Sensor Materials

Figure 2:
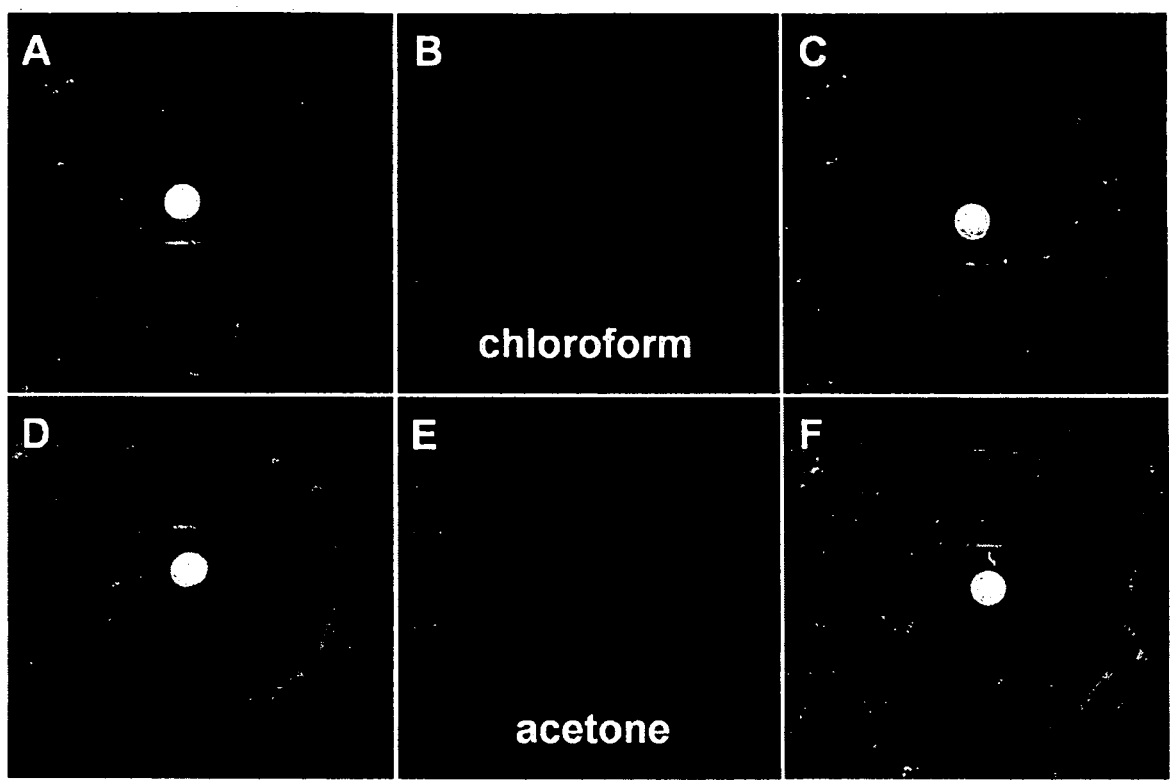
FIG. 2 shows photos of the HPS spots on the TLC plates in the Petri dish sets in the absence (A and D) and presence (B and E) of vapors of organic solvents and their recovery after removing the solvents (C and F).
Figure 3:
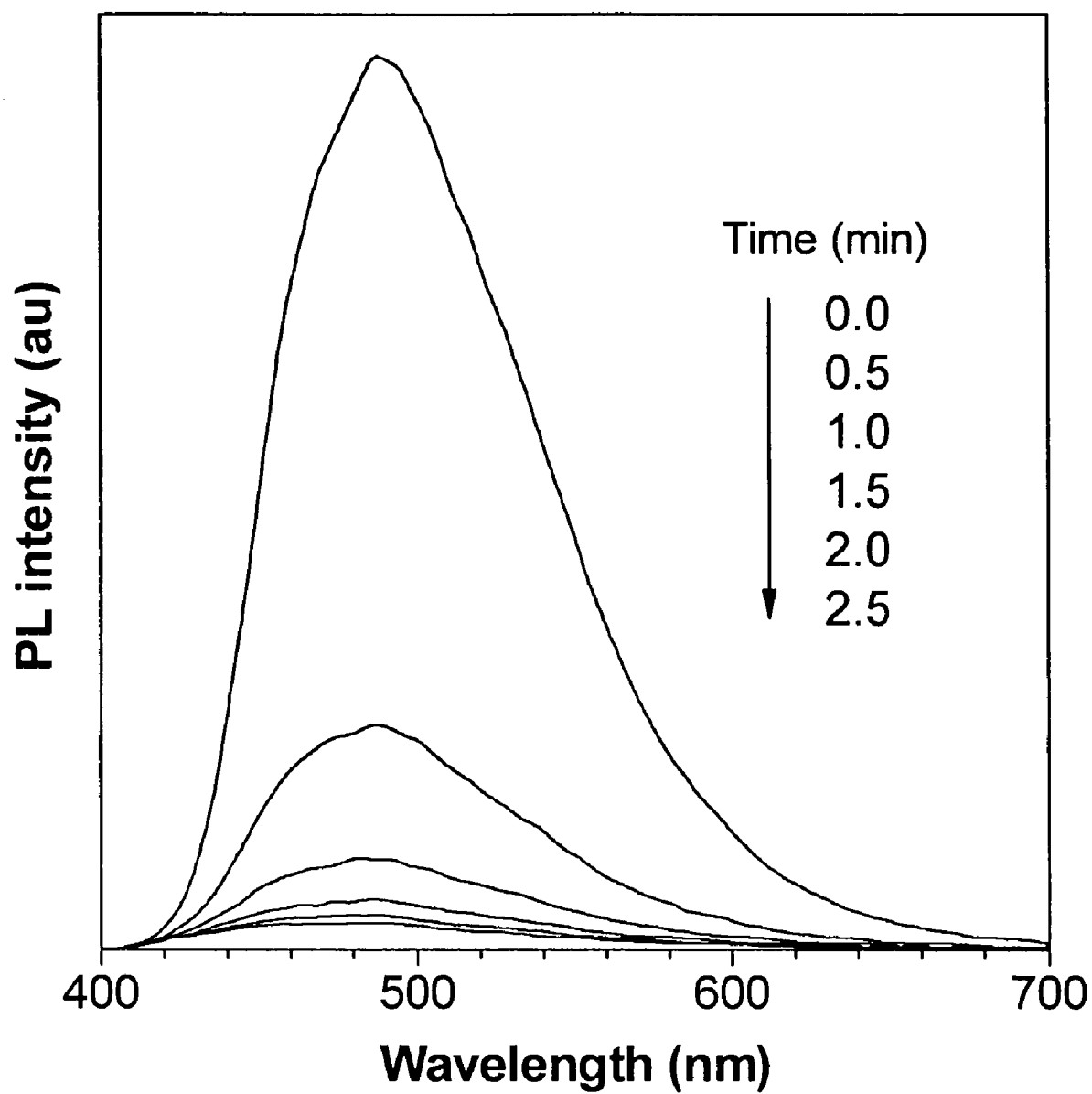
FIG. 3 presents the effect of the acetone vapor on the photoluminescence spectrum of a PMS film coated on a quartz cell at different time interval.

Under illumination of a 365-nm UV light at room temperature, dye nanoparticles on the TLC plate show bright blue fluorescence. The intense light emission quenches upon exposure to solvent vapors and becomes visibly emissive again when the solvents are purged. This process is complete reversible and the fluorescence can be fully recovered after the solvents have been removed. FIGS. 1 and 2 show photos of T2TPS and HPS spots, respectively, on the TLC plates in the Petri dish sets in the absence (A and D) and presence (B and E) of vapors of organic solvents and their recovery after removing the solvents (C and F). This quenching effect takes place in a rapid manner and can be quantified as shown in FIG. 3. The photoluminescence of a PMS film coated on a quartz cell almost completely quenches after 2 min of exposure to acetone vapor.

Figure 4:
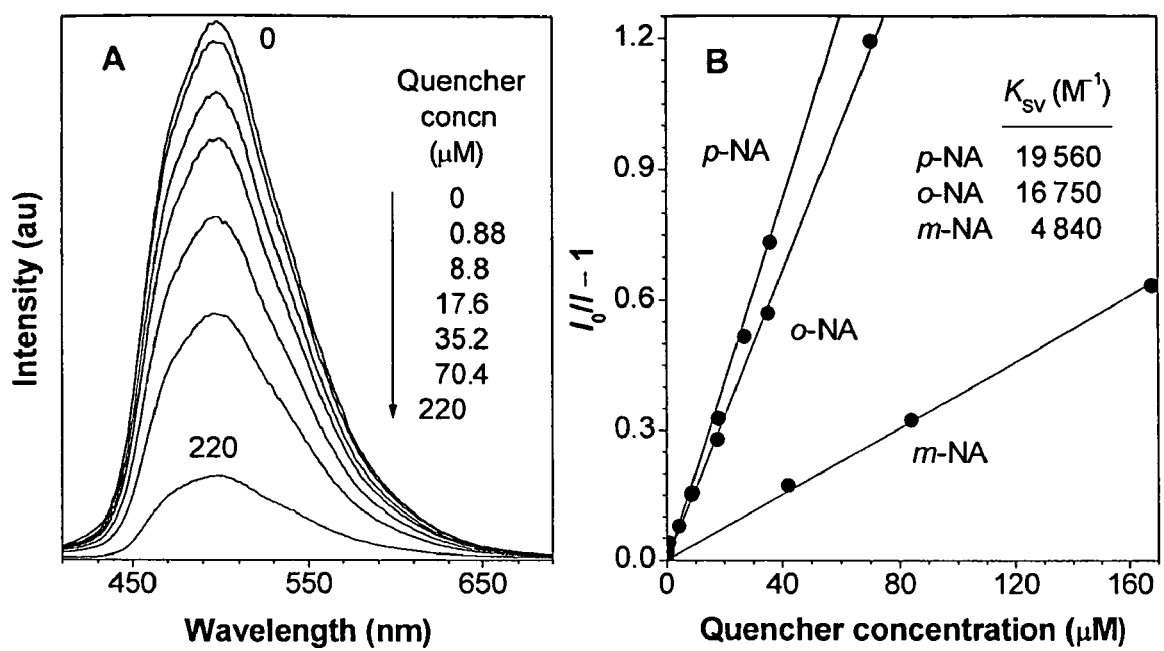
FIG. 4 shows the Quenching of PL of HPS-iP3,4 in THF by o-nitroaniline (o-NA) at various concentrations (A) and Stern-Volmer plots for the PL quenching of a THF solution of HPS-iP3,4 by o-, m- and p-NAs(B).

The sterically hindered molecules such as HPS-iP3,4 emit efficiently even in organic solution and spurred us to explore its potential application as a chemosensor. Nitroaromatics such as 2,4-dinitrotoluene (DNT) and 2,4,6-trinitrotoluene (TNT) are warfare explosives, detection of which has homeland-security and antiterrorism implications. Due to the commercial unavailability of these explosives, we used nitroanilines (NAs), a group of high-volume chemicals notorious for their "nitroaniline poisoning" and ecological hazard, as model compounds. The PL of HPS-iP3,4 weakens upon addition of o-NA into its solution (FIG. 4A) and its Stern-Volmer plot gives a quenching constant (KSV) as high as 16 750 M-1. The KSV varies when the regiostructure of the quencher changes, with KSV for the para isomer being ~4-fold higher than that for its meta counterpart, revealing that HPS-iP3,4 is capable of optically distinguishing the nitroaromatic regioisomers (FIG. 4B). The KSV values for quenching the PL of silole HPS-iP3,4 by the NAs are up to ~61-fold higher than those of the polysiloles by nitrobenzene, which is, like NA, also a mononitroaromatic. This high sensitivity is apparently associated with the high PL efficiency of HPS-iP3,4, while the regioisomeric discrimination is probably due to its selective interaction or preferred complexation with the analyte with a favorable electronic structure, noting that its PL quenching by p- or o-NA is more efficient than that by m-NA.

The discriminatory interactions between an emitter and a set of regioisomers with different electronic structures suggest that other highly luminescent species can also be used as sensitive optical probes to distinguish regioisomeric quenchers. We exploited this possibility. 9,10-Diphenylanthracene, for example, is an efficient blue-light emitter. Its KSV values for p-, o-, and m-NAs are very high with distinct difference, being 93 900, 53 500, and 10 200 M$^{-1}$, respectively. This clearly proves the generality of the regioisomeric detection by luminophoric molecules; in other words, PL quenching can be used as a general, versatile tool to sensitively and selectively recognize regioisomeric structures.

Figure 5:
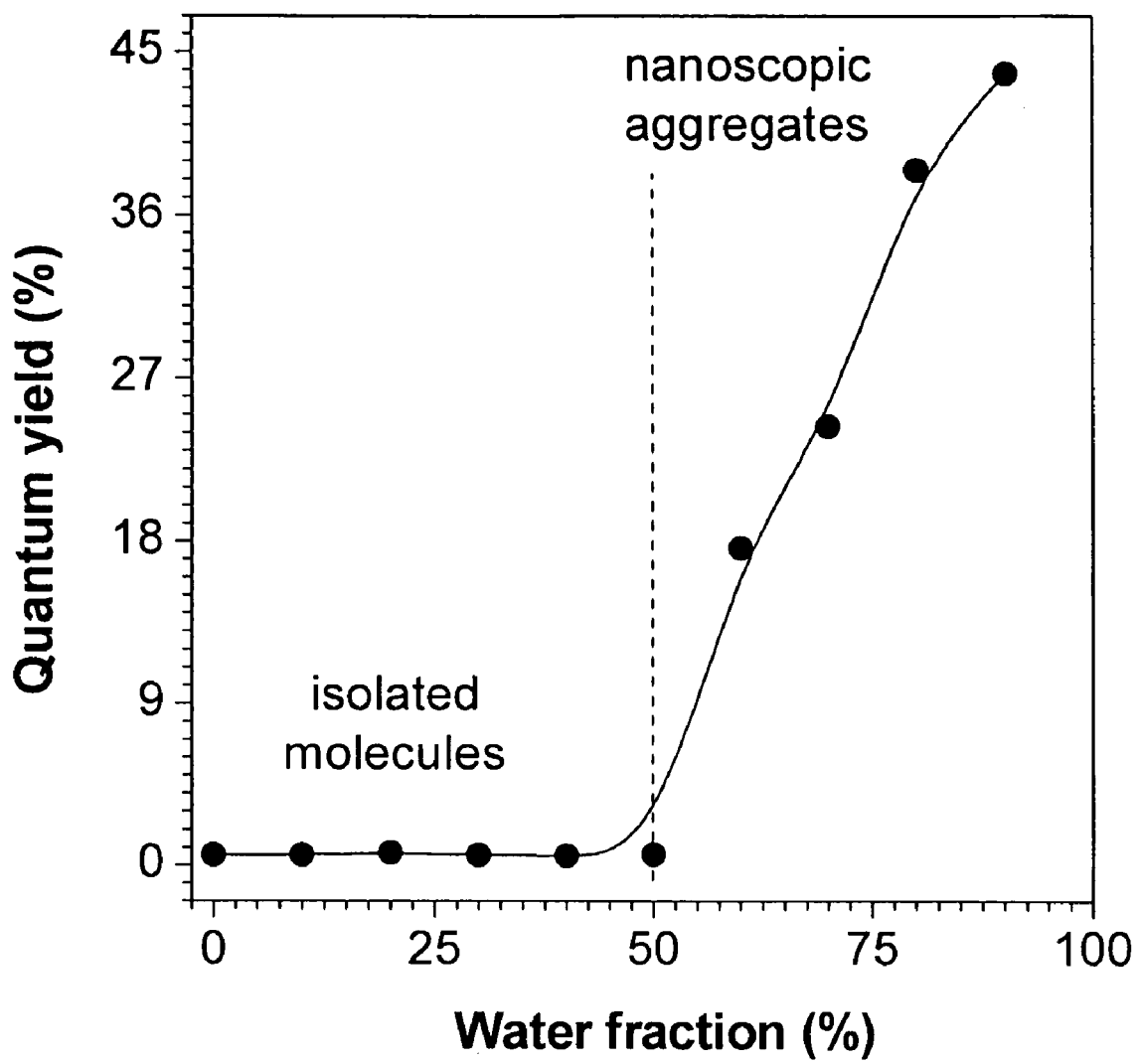
FIG. 5 shows an AIE effect of HPS-iP2,4: its quantum yield in water/acetone mixture versus the solvent composition.

Silole HPS-iP2,4 is weakly luminescent in solution but the AIE effect turns it into a strong fluorophore. When aggregated in, for example, a 90:10 water/acetone mixture, its $\Phi_{PL}$ is increased by ~80-fold to 43.8% (FIG. 5). The $\lambda_{max}$ of the nanoaggregate (473 nm) is blue-shifted from that of the solution (500 nm), which is abnormal because aggregation commonly red-shifts 80 $_{max}$. To double check this, we prepared a single crystal and amorphous film of HPS-iP2,4 by crystallization from its solution and by freezing its melt with liquid nitrogen, respectively. The aggregates in the crystal and film both show blue-shifted spectra, with their respective $\lambda_{max}$ values at 461 and 481 nm. The solid films of HPS-iP2,5 and HPS-iP3,4 (crystals unavailable; vide supra) also give blue-shifted spectra in comparison to those of their dilute solutions, confirming that the aggregation-induced blue shift is a general property of all the siloles. In the solid aggregates, the intramolecular rotation processes of the siloles are more restricted and the aryl peripheries may be more twisted from the central silole cores, in comparison to those in the dilute solutions. The former effect (enhanced rigidity) increases the luminescence efficiency, while the latter effect (reduced conjugation) may have blue-shifted the emission spectra.

Figure 6:
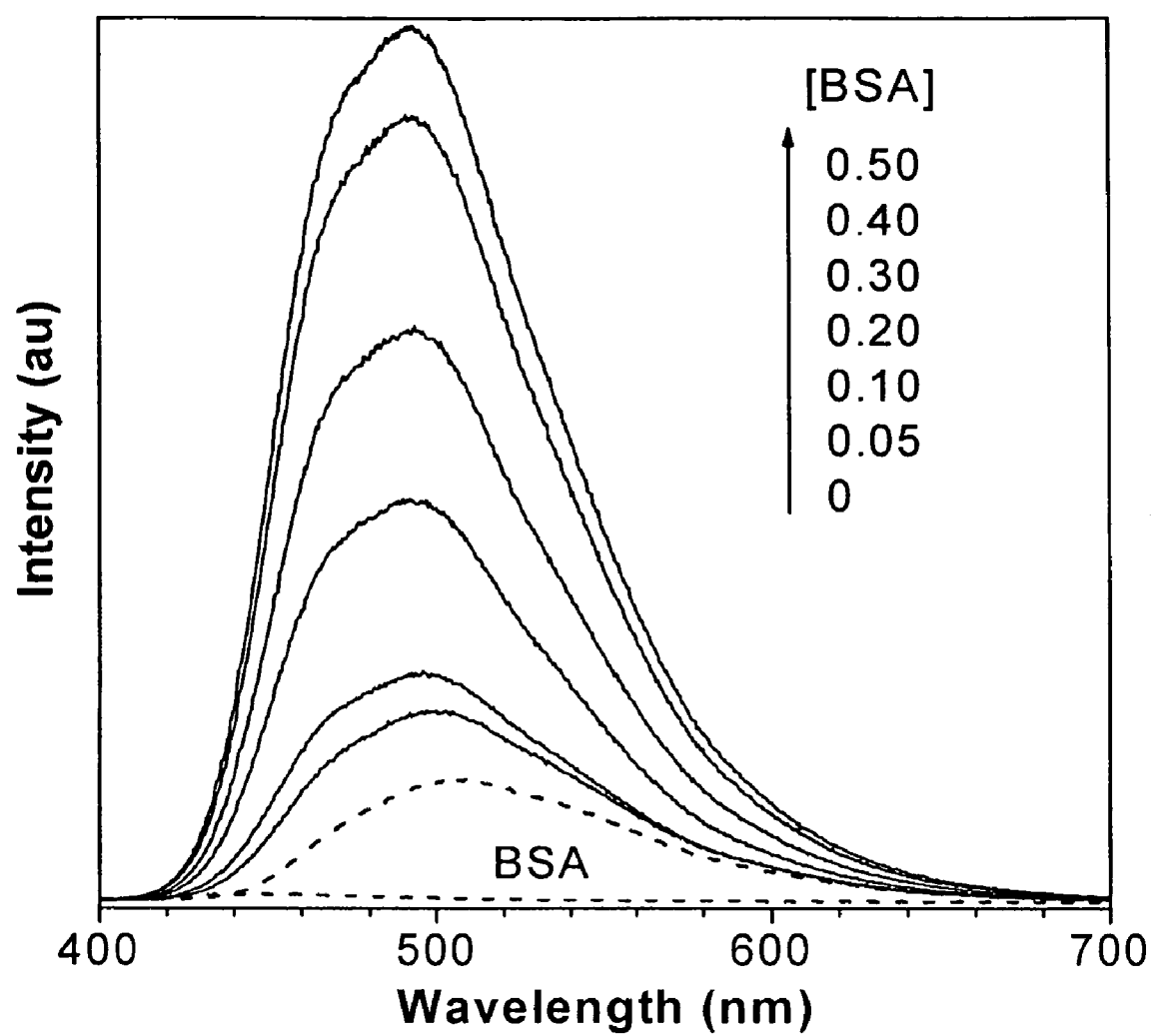
FIG. 6 is PL spectra of the water/methanol (6:4) solutions of a PPS—OH ($5.7 \times 10^{-5}$ M) in the presence of KOH ($8.4 \times 10^{-4}$ M) and BSA (at concentrations given in the figure).
Figure 7:
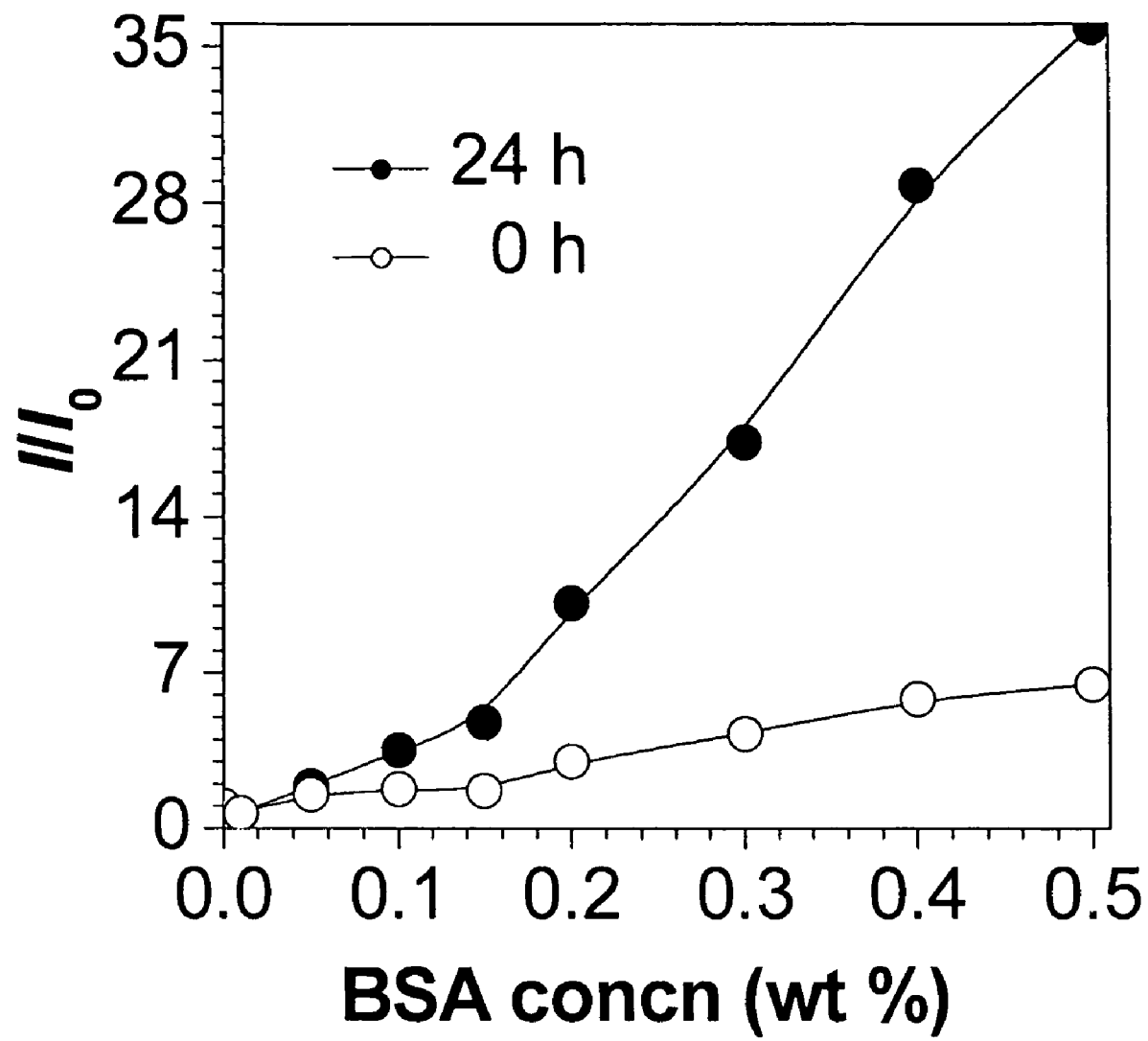
FIG. 7 shows the dependency of fluorescence intensity of PPS—OH on BSA concentration.

In order to utilize the dye molecules as biosensors in aqueous solutions, we prepared PPS-OH and tested its ability to detect bovine serum albumin (BSA). FIG. 6 depicts the PL spectra of the water/methanol (6:4) solutions of a PPS-OH in the presence of KOH and BSA at different concentrations. Clearly, with increasing amounts of BSA the PL intensity increases significantly. Upon prolonged standing the PL intensity enhances further, probably due to the more complete interaction of PPS-OH with BSA (FIG. 7).

Figure 8:
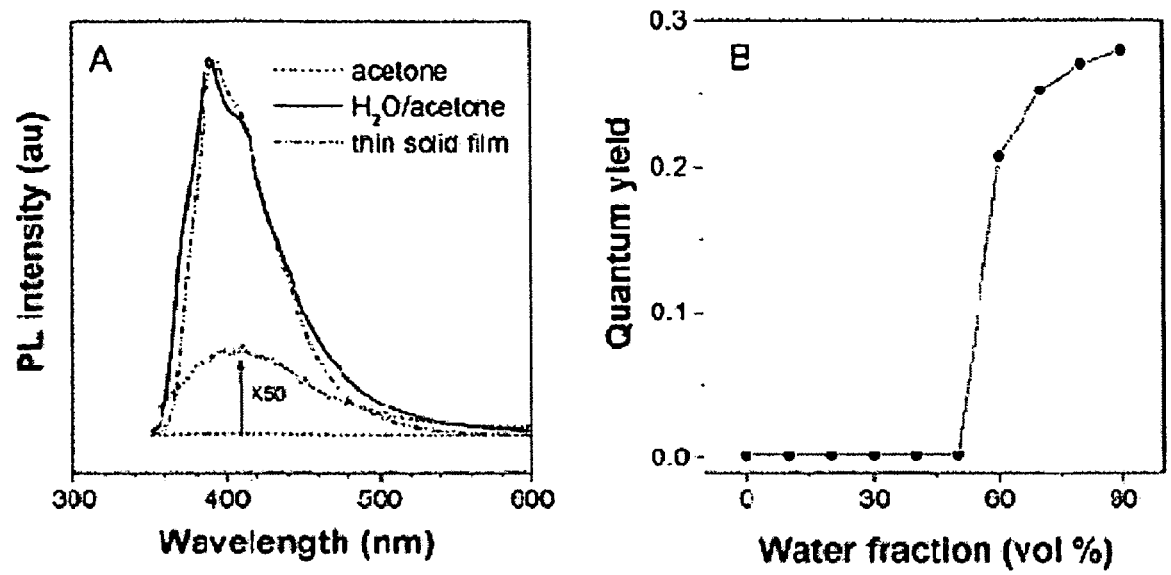
FIG. 8 is PL spectra of TPBD in acetone, TPBD in a water/acetone mixture (90:10 by volume), and its solid film (80 nm) (A); and PL quantum yield of TPBD vs. solvent composition of the water/acetone mixture (B).
Figure 9:
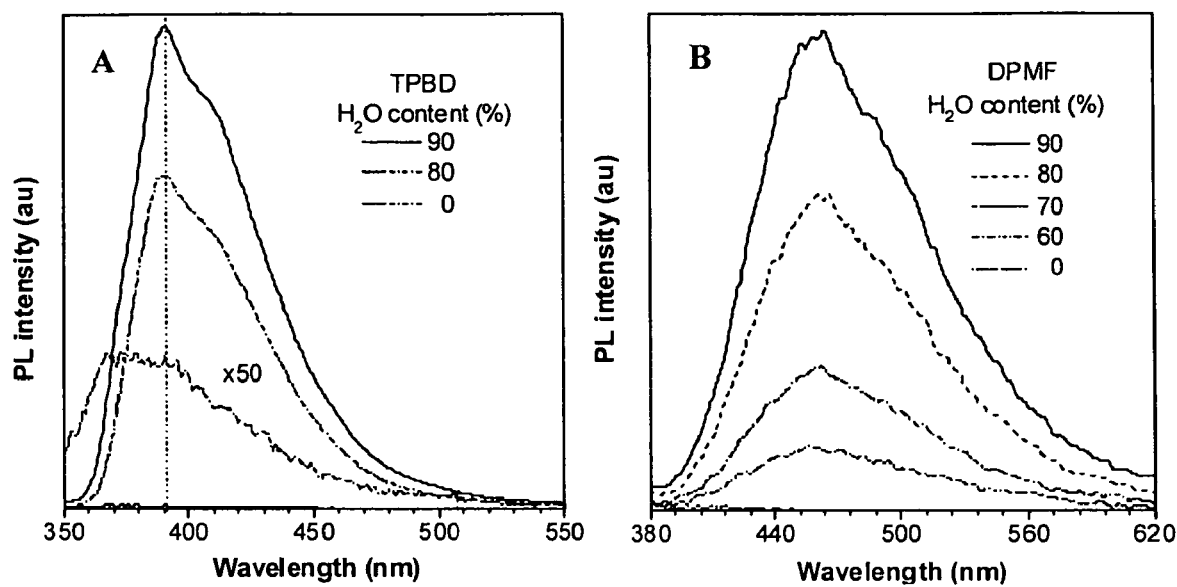
FIG. 9 is PL spectra of TPBD and DPMF in water/acetonitrile mixtures.
Figure 10:
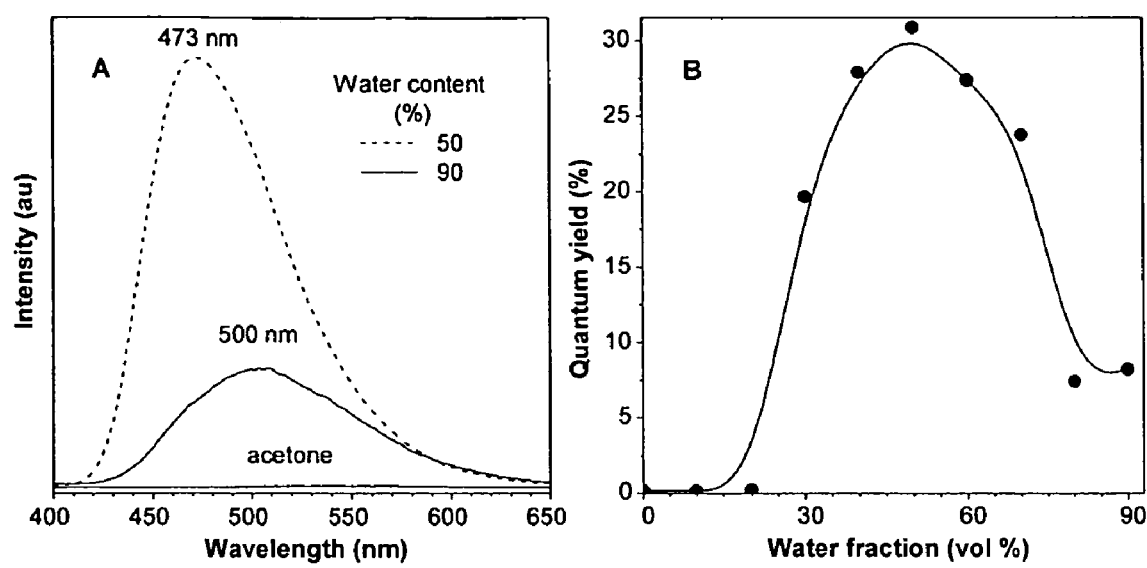
FIG. 10 is PL spectra of HPDMCB in absolute acetone and water/acetone mixtures; concentration (A) and quantum yield vs. solvent composition of water/acetone mixture (B).

Not only the silole but also dye molecules consisting of double bonds connected to aromatic rings show luminescence enhancement depending on their chemically environment. Similar to silole derivatives, TPBD shows the aggregation-induced emission (AIE) phenomena. That is: the pure organic solution (acetone) of TPBD fluoresces only weakly but become much stronger upon addition of a non-solvent (water) or in solid film (FIG. 8). Likewise, upon addition of large amounts of poor solvent (water) into the acetonitrile solutions of TPBD and DPMF the light emissions of the dyes are boosted, similar to that observed in the T2TPS system. While the emission maximum of TPBD is at 390 nm (FIG. 9A), DPMF exhibits a steady luminescence increase with its maximum at 460 nm (FIG. 9B). Unlike T2TPS, no shifts in their emission peaks are observed. The PL of HPDMCB in the acetone/water mixtures increases with an increase in the water content, with $\lambda_{max}$=470 nm for solutions containing 50 and 70% water (FIG. 10). Further increase in the nonsolvent fraction leads again to a more than 30 nm red shift in the PL spectrum. The reason for this different emission behavior might be due to the different crystallization and packing ability of these compounds. While TPBD and DPMF are relatively small and therefore have no difficulties to pack in a thermodynamic favorable arrangement, T2TPS and HPDMCB are sterically bulky, leading to kinetically controlled aggregation of the dye molecules under the same experimental conditions.

Figure 11:
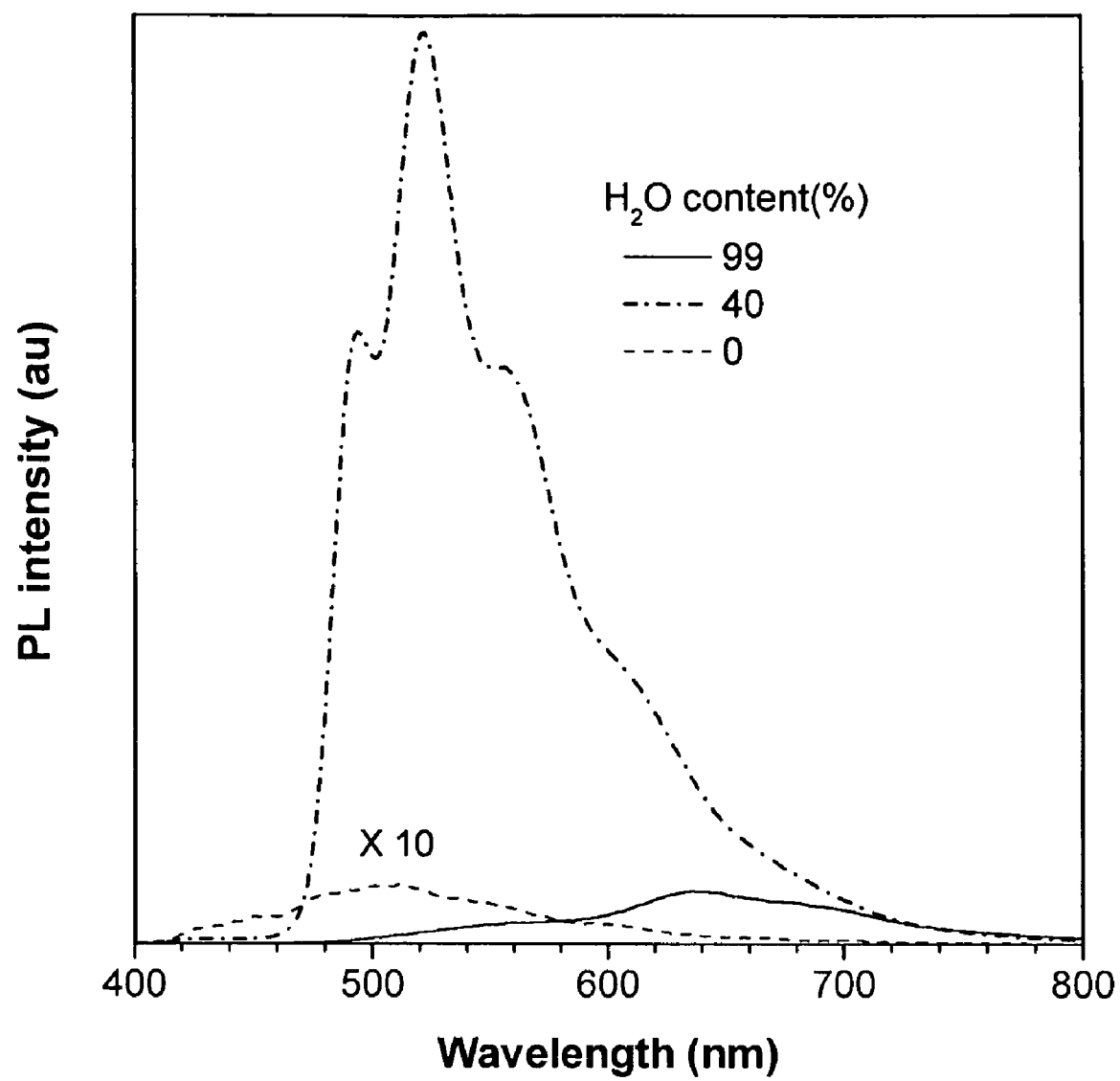
FIG. 11 is photoluminescence spectra of SCholP in THF/water mixtures.

Unlike previous compounds, SCholP contains a chiral cholesterol moiety, which may impart new chromophoric features such as polarized light emission. FIG. 11 shows the PL spectra of a dilute THF solution of SCholP. The emission is very weak with its emission maximum centered at 508 nm. The addition of water boosts the fluorescence and an intense green emission of 523 nm can be observed at a water content of 40%. Further increase of the water content to 99% (while keeping its concentration constant) decreases the emission intensity but shifts its maximum dramatically for more than 100 nm to 640 nm, turning SCholP from a green to a red emitter. Similar to T2TPS and HPDMCB, the packing of the SCholP molecules will have influenced its fluorescence properties. When the water content is increased to ~40%, the majority of the SCholP molecules starts to aggregate into nanocrystals with intense green light emission. Since the THF content is high enough, the molecules can align properly and crystallize slowly (thermodynamically controlled). In contrast, at a water content of as high as 99%, the particles will cluster very quickly, resulting in a random or kinetically controlled order. Just as we have speculated, the emitted green light of SCholP is a polarized emission (with the polarization value ~0.446). However, the red light of the solution with a water content of 99% is a normal isotropic emission. This becomes immediately clear if the previous findings are considered. The controlled packing of the SCholP molecules may lead to a formation of a helical structure, due to the combination of the pyranylidene malonitrile head group, with its large dipole moment, and the chiral cholesterol groups, which results in the polarized green emission. Meanwhile, the addition of large amounts of nonsolvent leads to an uncontrolled aggregation, which may not allow such a highly ordered secondary structure to form and will thus yield a normal isotropic emission.

In the foregoing description of the invention, there is no intention to be bound by any expressed or implied theory presented in explaining the properties of the conjugated polyenes.

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended claims.

What is claimed is:

1. A sensor device for detecting the presence or absence of a target molecule or substance, comprising a holder and a detecting molecule being held in place by said holder and being accessible to said target molecule or substance, said detecting molecule comprising a chemically conjugated system of at least 6 conjugated double bonds and a backbone structure of a formula selected from the group consisting of:

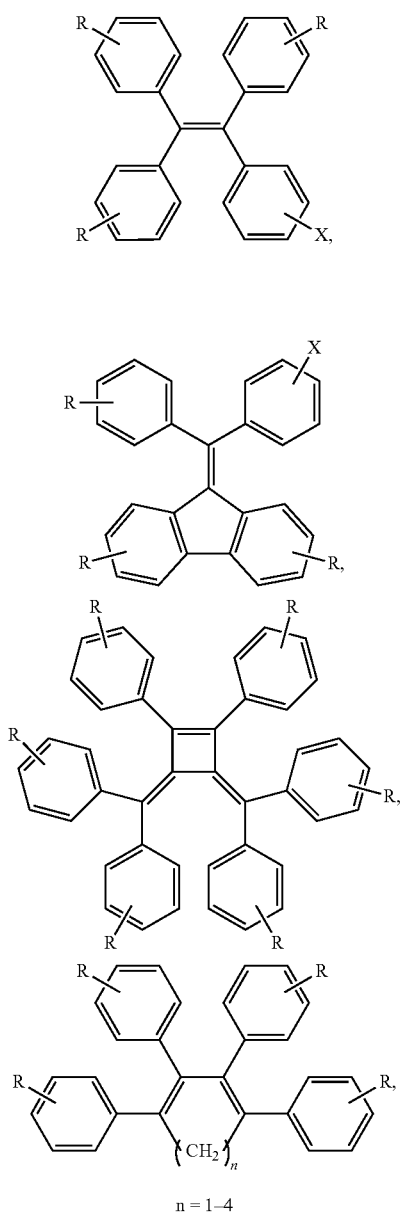

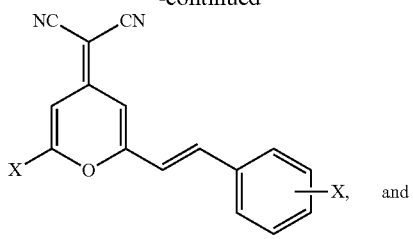

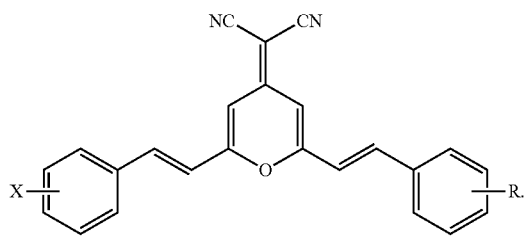

wherein R is a substituent independently selected from the group consisting of H, C(O)R, COOR, $BR_2$, $SiR_3$, $GeR_3$, $NR_2$, $PR_2$, $P(O)R_2$, OR, SR, SeR, alkyl, unsaturated alkyl, heteroalkyl, cycloalkyl, heterocycloalkyl, aryl, and heteroaryl and X is a substituent independently selected from the group consisting of C(O)R, COOR, $BR_2$, $SiR_3$, $GeR_3$, $NX_2$, $PR_2$, $P(O)R_2$, OX, SR, SeR, alkyl, unsaturated alkyl, heteroalkyl, cycloalkyl, heterocycloalkyl, aryl, and heteroaryl wherein said X, alkyl, unsaturated alkyl, heteroalkyl, cycloalkyl, heterocycloalkyl, aryl, and heteroaryl are independently either substituted or unsubstituted and contain more than 4 carbon atoms.

2. A sensor device for detecting the presence or absence of a target molecule or substance, comprising a holder and a detecting molecule being held in place by said holder and being accessible to said target molecule or substance, said detecting molecule comprising a chemically conjugated system of at least 6 conjugated double bonds and of a formula selected from the group consisting of:

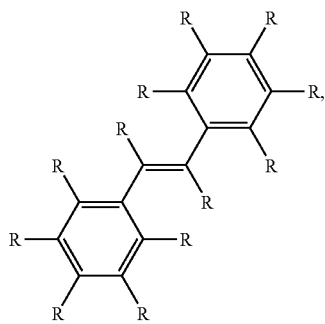

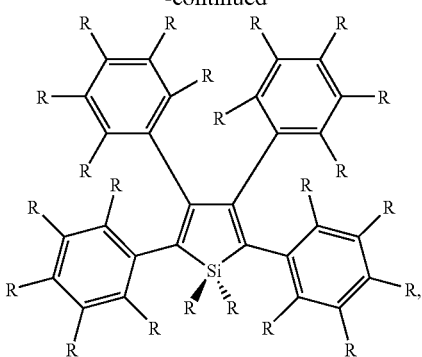

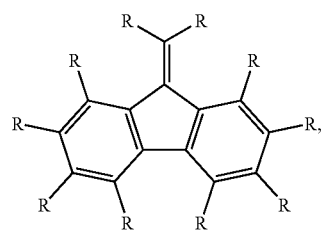

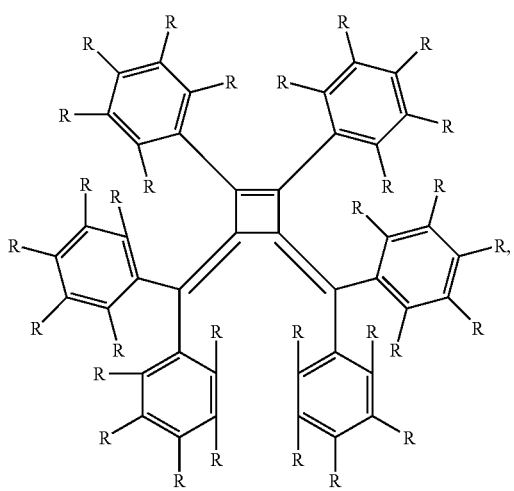

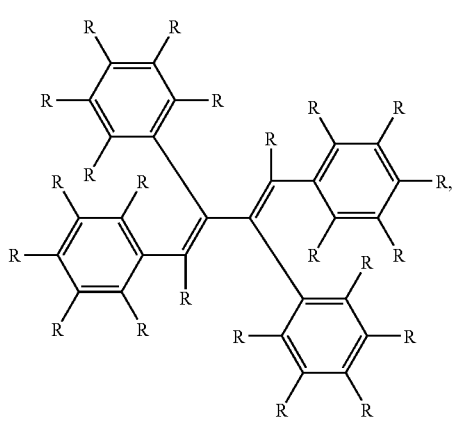

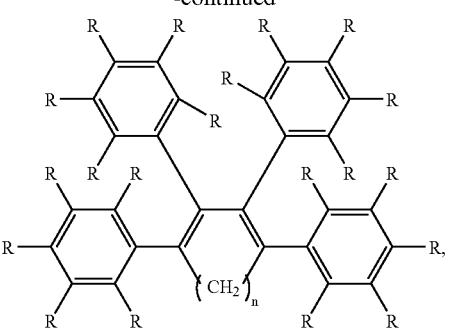

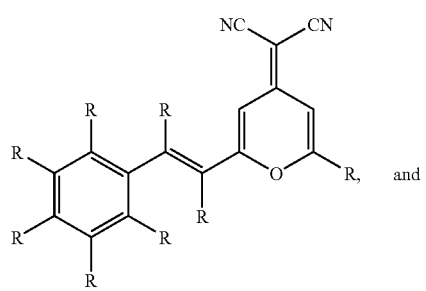

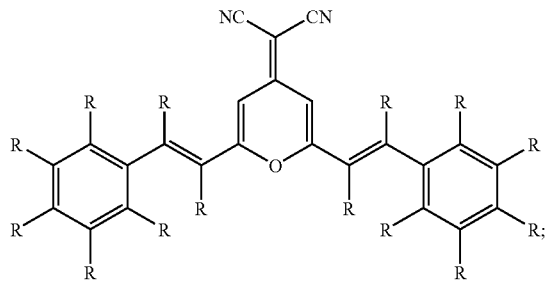

wherein R is a substituent independently selected from the group consisting of H, C(O)R, COOR, BR$_2$, SiR$_3$, GeR$_3$, NR$_2$, PR$_2$, P(O)R$_2$, OR, SR, SeR, alkyl, unsaturated alkyl, heteroalkyl, cycloalkyl, heterocycloalkyl, aryl, and heteroaryl wherein said alkyl, unsaturated alkyl, heteroalkyl, cycloalkyl, heterocycloalkyl, aryl, and heteroaryl are independently either substituted or unsubstituted.

3. A compound for detecting the presence or absence of a target molecule or substance comprising a chemically conjugated system of at least 6 conjugated double bonds and, comprising a backbone structure of a formula selected from the group consisting of:

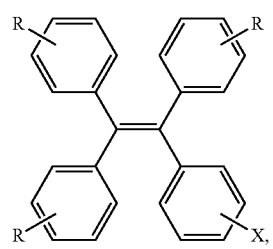

-continued

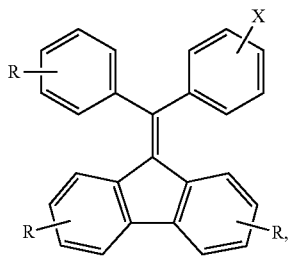

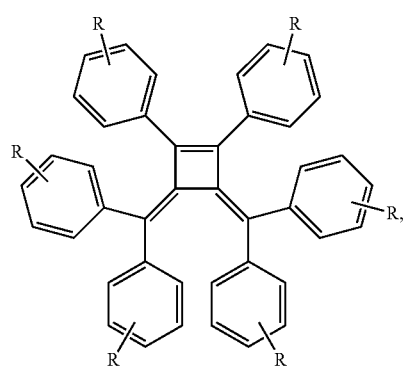

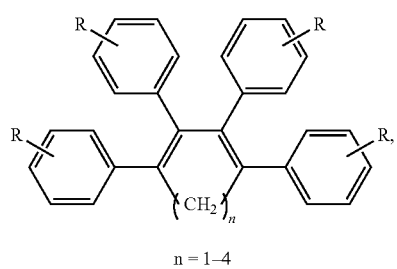

n = 1-4

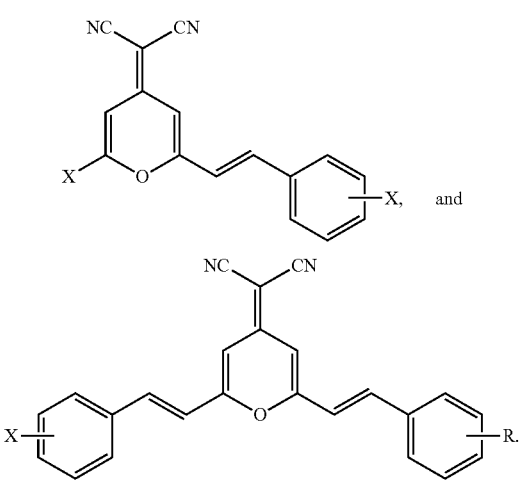

wherein R is a substituent independently selected from the group consisting of H, C(O)R, COOR, $BR_2$, $SiR_3$, $GeR_3$, $NR_2$, $PR_2$, $P(O)R_2$, OR, SR, SeR, alkyl, unsaturated alkyl, heteroalkyl, cycloalkyl, heterocycloalkyl, aryl, and heteroaryl and X is a substituent independently selected from the group consisting of C(O)R, COOR, $BR_2$, $SiR_3$, $GeR_3$, $NX_2$, $PR_2$, $P(O)R_2$, OX, SR, SeR, alkyl, unsaturated alkyl, heteroalkyl, cycloalkyl, heterocycloalkyl, aryl, and heteroaryl wherein said X, alkyl, unsaturated alkyl, heteroalkyl, cycloalkyl, heterocycloalkyl, aryl, and heteroaryl are independently either substituted or unsubstituted and contain more than 4 carbon atoms.

4. The compound of claim 3, wherein said backbone formula is:

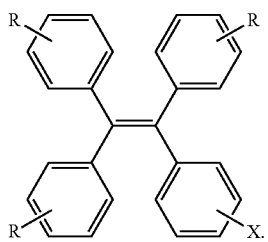

5. The compound of claim 3, wherein said backbone formula is:

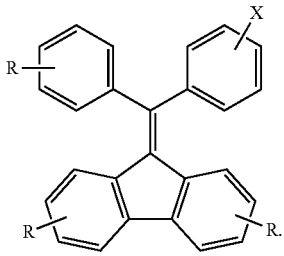

6. The compound of claim 3, wherein said backbone formula is:

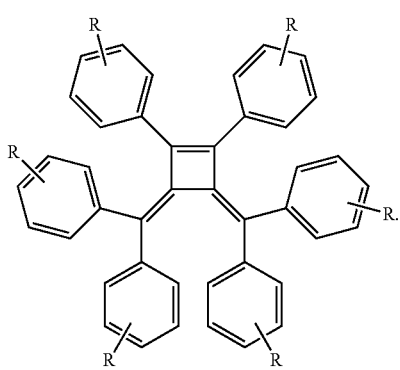

7. The compound of claim 3, wherein said backbone formula is:

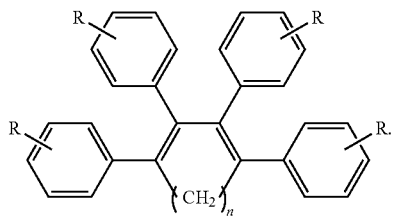

n = 1–4

8. The compound of claim 3, wherein said backbone formula is:

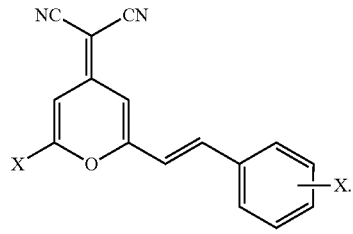

9. The compound of claim 3, wherein said backbone formula is:

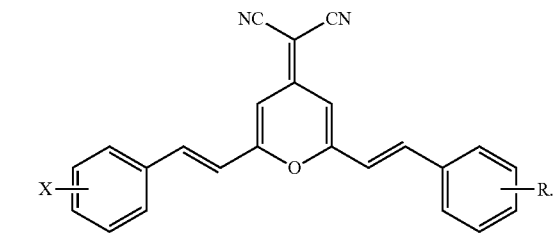

10. The compound of claim 3, being selected from the group consisting of:

DcholP, ScholP, PoAcAmMF, PoAnMF and A2HPS.

11. The compound of claim 3, being selected from the group consisting of:

PES, HPS-iP2,4, HPS-iP2,5, HPS-iP3,4 and T2TPS.

* * * * *